United States Patent [19]

Hagiwara et al.

[11] Patent Number: 5,804,408
[45] Date of Patent: Sep. 8, 1998

[54] EXPRESSION OF HUMAN SOD IN BLUE GREEN ALGAE

[75] Inventors: Hideaki Hagiwara, Takarazuka; Yasunobu Takeshima, Kasai, both of Japan

[73] Assignee: Yoshihide Hagiwara, Takarazuka, Japan

[21] Appl. No.: 368,236

[22] Filed: Jan. 3, 1995

Related U.S. Application Data

[63] Continuation of Ser. No. 941,139, filed as PCT/JP92/00289, Mar. 11, 1992, abandoned.

[30] Foreign Application Priority Data

Mar. 13, 1991 [JP] Japan .................... 3-073905

[51] Int. Cl.$^6$ .................... C12P 21/00; C12N 15/70; C12N 15/63; C07H 21/02
[52] U.S. Cl. .................... 435/69.1; 435/172.3; 435/252.3; 435/320.1; 435/946; 536/23.2; 536/24.1; 935/6; 935/29; 935/41; 935/56
[58] Field of Search ............... 435/69.1, 172.3, 435/252.3, 320.1, 946; 536/23.2, 24.1; 935/6, 29, 41, 56, 66

[56] References Cited

U.S. PATENT DOCUMENTS

| | | | |
|---|---|---|---|
| 4,742,004 | 5/1988 | Hartman et al. | 435/189 |
| 5,066,591 | 11/1991 | Hallewell et al. | 435/189 |

FOREIGN PATENT DOCUMENTS

| | | |
|---|---|---|
| 1216531 | 1/1987 | Canada . |
| 130684 | 8/1985 | Japan . |
| 273473 | 1/1988 | Japan . |
| 210129 | 2/1988 | Japan . |
| 156884 | 12/1988 | Japan . |
| 8806631 | 9/1988 | WIPO . |

OTHER PUBLICATIONS

Takeshima et al., "High–level expression of Human Superoxide Dismutase in the Cyanobacterium *Anacystis nidulans* 6301", Proceedings of the National Academy of Sciences (USA), vol. 91, No. 21, pp. 9685–9689, 1994.
Takeshima et al., "A Novel Expression Vector for the Cyanobacterium, Synechococcus PCC 6301", DNA Research, vol. 1, pp. 181–189, 1994.
Scanlan et al. (1990) Gene, vol. 90, pp. 43–49.
Schaefer et al. (1989) Journal of Bacteriology, vol. 171, pp. 3973–3981.
Shinozaki et al. (1985) Molecular and General Genetics, vol. 200, pp. 27–32.
Barra et al. (1980) FEBS Letters, vol. 120, pp. 53–55.
Guarente et al. (1980) Science, vol. 209, pp. 1428–1430.
Shinozaki et al. (1982) Gene, vol. 19, pp. 221–223.

*Primary Examiner*—W. Gary Jones
*Assistant Examiner*—Jeffrey Fredman
*Attorney, Agent, or Firm*—Sherman and Shalloway

[57] ABSTRACT

A method for expressing a physiologically active polypeptide in cells of a blue-green alga by transforming the cells of a blue-green alga with a recombinant DNA containing a structural gene encoding the polypeptide, characterized in that as the recombinant DNA is used a recombinant DNA which contains a structural gene encoding the physiologically active polypeptide, the transcription initiation region of the RuBisCO gene of *Anacystis nidulans* located upstream of the structural gene, and the transcription termination region of the RuBisCO gene located downstream of the structural gene. According to this method, physiologically active polypeptide can efficiently be expressed using blue-green algae.

21 Claims, 10 Drawing Sheets

Synthesized phosphorylated oligonucleotides

FIG. 6
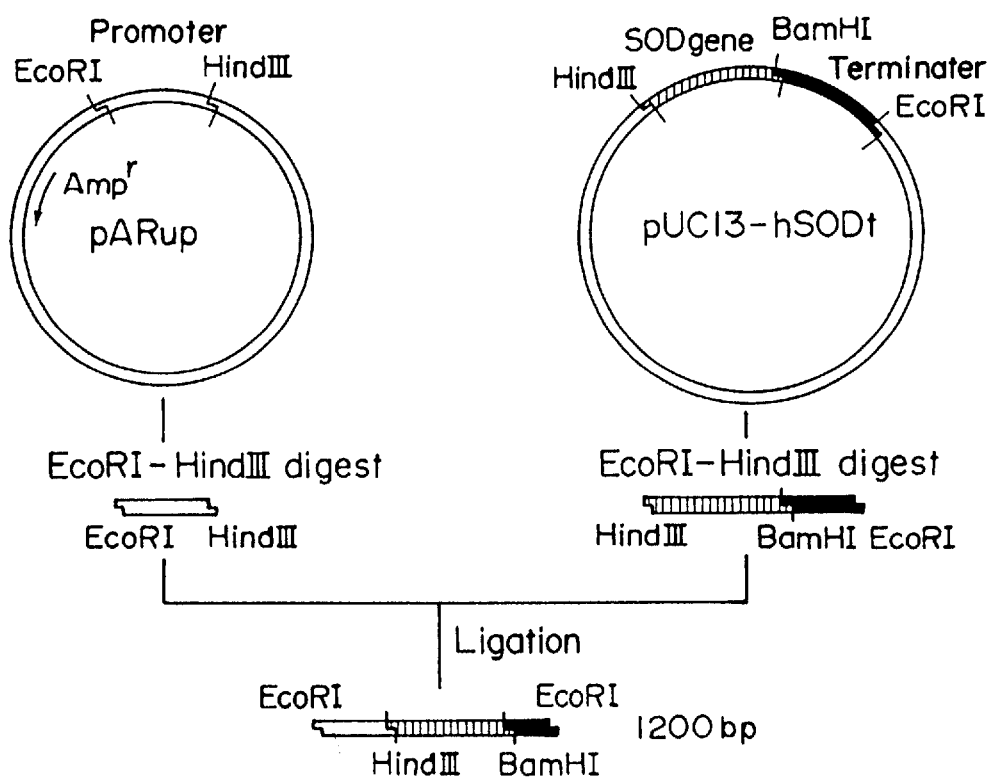
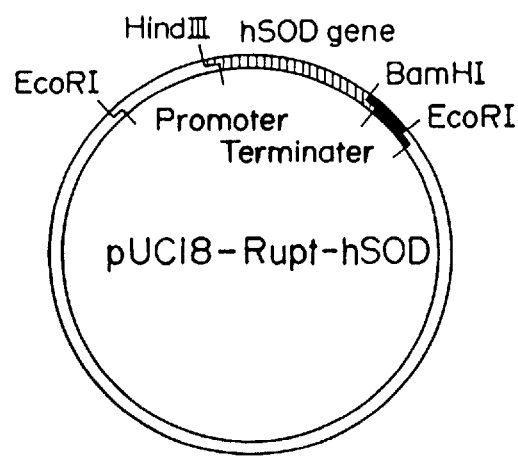

FIG. 7a

```
         10         20         30         40         50         60         70
GAGCTCCCCA ATCCTCGTGA TGATCAGTGA TGGAAAAAGC ACTGTAATTC CCTTGGTTTT TGGCTGAAAG 80         90        100        110        120        130        140
TTTCGGACTC AGTAGACCTA AGTACAGAGT GATGTCAACG CCTTCAAGCT AGACGGGAGG CGGCTTTTGC 150        160        170        180        190        200        210
CATGGTTCAG CGATCGCTCC TCATCTTCAA TAAGCAGGGC ATGAGCCAGC GTTAAGCAAA TCAAATCAAA
                                                              Transcription initiation point
        220        230        240        250        260        270        280
TCTCGCTTCT GGG|CTTTCAAT AAATGGTTCC|GATTGATGAT AGGTTG|ATTC ATGAGGAATC TAAGGCTTAA
                -35 region                          -10 region      ↱

290        300        310        320        330        340        350
TTCTCCACAA AAGAATTAAG CGTCCGTCGC AACGGAAGTC TCCGCTGGAC TTGCGCTGTG GGACTGCAGC 360        370        380        390        400        410        420
TTTACAGGCT CCCCCCTGCCA GAAATCCTGA ATCGTCGACC ATATCTGACA TATCTCTAGG GAGAAAGCTT
                                                                    S/D 430        440        450        460        470        480        490
ATGGCTACCA AAGCTGTTTG CGTTCTGAAA GGTGACGGCC CGGTTCAGGG TATCATCTTC GAACAGAAAG 500        510        520        530        540        550        560
AATCTAACGG TCCGGGTTAAA GTTTGGGGTT CTATCAAAGG CCTGACCGAA GGTCTGCATG GATTCCATGT 570        580        590        600        610        620        630
TCATGAATTT GGTGACAACA CTGCAGGTTG CACCCTCTGCA GGGCCTCATT TCAACCCGCT GTCGCGTAAA 640        650        660        670        680        690        700
CATGGTGGGC CGAAAGACGA AGAACGTCAT GTTGGTGACC TAGGTAACGT TACCGCTGAC AAAGACGGTG
```

FIG. 7b

```
710              720              730              740              750              760              770
TCGCTGACGT  TTCTATCGAA  GACTCTGTTA  TCTCTCTGTC  TGGTGACCAT  TGCATCATCG  GTCGTACTCT 780              790              800              810              820              830              840
GGTTGTTCAT  GAAAAAGCGG  ATGACCTGGG  TAAAGGTGGT  AACGAGGAAT  CTACCAAAAC  CGGTAACGCT 850              860              870              880              890              900              910
GGTTCTCGTC  TGGCATGCGG  TGTTATCGGT  ATCGCTCAGT  AGTGAGGATC  CCGGGCCGCTA  CTAAAGCCTG
                                                Stop Stop 920              930              940              950              960              970              980
ATTTGTCTTG  ATAGCTGCTC  TGCCCTTTGGG  CAGGGGCTTT  TTTCTGTCTG  CCATTCTTGA  GGATGGGCGGA 990              1000             1010             1020             1030             1040             1050
CTCTTTCCCT  TTTGCTCTAC  GCCCATGAAT  GCGATCGCAG  TCTCCCCTGT  CCAGCACGTT  GGAGTGATTG
C 1060             1070             1080             1090             1100             1110             1120
GTGGTGGCCA  GTTAGCTTGG  AGTCTGGCAC  CAGCAGGCA  ACAGTTGCGG  ATGTCGCTGC  ACGTTCAAAC 1130             1140             1150             1160             1170             1180
ACCCAATGAT  CACGACCCAG  CGCGGATCAA  ACCGTATTGC  AAGCAGTTGC  TGACGC
           Transcription termination point
```

Strain R2
pBAXSOD
Cont. 6-4 8-4 hSOD

Endogenous Fe-SOD

Strain R2
pBAX
SOD6-4 Cont. hSOD

Strain R2
pBAXSOD
6-4 hSOD (A)  Cont.

8-4
pBAXSOD
Strain R2

A = anti-hSOD 5,804,408

EXPRESSION OF HUMAN SOD IN BLUE GREEN ALGAE

This application is a continuation of application Ser. No. 07/941,139, filed as PCT/JP92/00289, Mar 11, 1992, abandoned.

TECHNICAL FIELD

This invention relates to a method for expressing polypeptides, and relates more detailedly to a method for expressing efficiently a physiologically active polypeptide by using cells of a blue-green alga as a host and transforming them with a carrier DNA containing a structural gene encoding the polypeptide.

BACKGROUND TECHNIQUES

Blue-green algae (also called cyanobacteria), like *Escherichia coli* etc., are procaryotes having no nuclear membrane. However, blue-green algae have a photosynthesis system similar to that of higher plants, especially red algae, and can, using light from the sun as an energy source, biosynthesize organic substances from water and carbon dioxide and slight amounts of inorganic salts and autotrophically proliferate in a large amount.

Further, many species of blue-green algae have long been known to be safely ingested (Spirulina, Aphanothece, Nostoc, etc.), and have not been reported for pathogenicity and parasitic properties on animals. Therefore, blue-green algae are suitable as hosts for genetic recombination and excellent also in safety.

If it becomes possible to introduce into blue-green algae having the above characteristics genes encoding useful physiologically active peptides and express them in a large amount, it is possible to produce food, functional food, feed, etc. without being influenced by seasons and weather as in the case of crops, and it can be expected that it becomes possible to produce medicinal drugs, chemicals not included in medicinal drugs, but used in medical treatment, raw materials for cosmetics, etc. in a low cost and low energy and economically in a source aspect.

Recently, development of host-vector systems using blue-green algae has rapidly progressed and expression of many heterogenous protein genes has been reported using species such as *Anacystis nidulans* R2 (Synechococcus PCC 7942), *Agmenellum quadruplicatum* (Synechococcus PCC 7002), Synechocystis PCC 6803 and Anabaena PCC 7120 [refer to G. D. Price and M. R. Badger, Plant Physiol, 91:505–513 (1989) on expression of human carbonic anhydrase and the lac $I_Q$ repressor protein of *Escherichia coli;* R. de Lorimier et al., J. Bacteriol, 169:1830–1835(1987) on expression of allophycocyanin of a higher alga *Cyanophora paradoxa;* I. V. Elanskaya and I. B. Morzunova, Mol. Genet. Mikrobiol. Virusol, 0(9):7–11 (1989) on expression of α-amylase of *Bacillus amylolique-faciens* A50; N. Tandeau de Marsac et al., Mol. Gen. Genet. 209:396–398(1987) on expression of an insecticidal protein of *B. shaericus* 1593M; C. Angsuthanasombat and S. Panyim, Appl. Environ. Microbid. 55:2428–2430(1989) on expression of the 130 kDa δ-endotoxin of *B. thuringiensis* var. *israelensis;* Y. Cai and C. P. Wolk, J. Bacteriol, 172:3138–3145(1990) on expression of levansucrase of *B. subtilis;* G. Schmetterer et al., J. Bacteriol, 167:411–414 (1986) on expression of luciferase of *Vibrio harvei* and *V. fischeri;* D. J. Scanlan et al., Gene 90:43–49 (1990), M. R. Schaefer and S. S. Golden,. J. Bacteriol, 171:3973–3981(1989) and J. S. Buzby et al., Science 230:805–807(1985) on expression of β-galactosidase of *Escherichia coli;* D. A. Lightfoot et al., Plant Mol. Biol, 11:335–344(1988) on expression of glutamate dehydrogenase of *Escherichia coli;* R. C. Murphy et al., J. Bacteriol, 172:967–976(1990) on expression of the rec A protein of *Escherichia coli;* M. Y. Gruber et al., Proc. Natl. Acad. Sci. USA 87:2608–2612(1990) on expression of Mn-superoxide dismutase of *Escherichia coli;* J. Pierce et al., Proc. Natl. Acad. Sci. USA 86:5753–5757(1989) on expression of RuBisCO of a photosynthesis bacterium *Rhodospirillum rubrum;* D. Friedberg and J. Seijffers, Mol. Gen. Genet. 203:505–510(1986) on expression of the cI repressor protein of bacteriophage λ].

However, in many of the above reports, the transcription initiation region of the gene itself of the host is used as such for expression of the gene encoding the heterogeneous protein, and the amount of the expressed desired protein is very slight. Further, in the report wherein a heterogeneous protein (human carbonic anhydrase, phase λcI repressor) was expressed using the tac promoter or $O_L P_L$ promotor, in order to increase the amount of the desired protein to be expressed, a contrivance was made, for example, of introducing genes encoding the control proteins of these promoters into the same vector, too. However, even in the case of human carbonic anhydrase whose expressed amount was disclosed in the report, the expressed amount is small and only about 0.3% of the soluble proteins, and such expression amount as was expected cannot be obtained.

On the other hand, reports are made wherein a transcription initiation region of a host blue-green alga is used as a transcription initiation region for expression of a heterogenous protein (β-galactosidase of *Escherichia coli*) [supra Gene 90:43–49(1990) and J. Bacteriol. 171:3973–3981 (1989)]. However, in each case, since the β-galactosidase gene is introduced into the structural gene of the blue-green alga, the β-galactosidase gene is expressed as a fused protein and thus there remains a problem in the point of production of the desired heterogeneous protein.

Thus, in order to efficiently express a physiologically active protein using a blue-green alga as a host cell, the present inventors, first, ligated the transcription initiation region and transcription termination region of the RuBisCO (ribulose-1,5-diphosphate carboxylase/oxygenase ) gene of *Anacystis nidulans* to a structural gene whose expression was intended, and intensely studied using the resulting ligate for preparation of an operon functioning in a blue-green alga. As a result, they found that the structural gene is efficiently expressed by using the transcription initiation region and transcription termination region of RuBisCO and that the expression amount is also influenced according to the kind of vector into which the prepared operon is introduced.

Further, they found that the base number of from the SD (Shine-Delgarno) sequence about which some report had been made in *Escherichia coli*, etc. to ATG (translation initiation site) has an influence on expression of the structural gene, succeeded in remarkably enhancing its expression amount by optimization of the base number, and completed this invention.

DISCLOSURE OF THE INVENTION

Thus, according to this invention there is provided a method for expressing a physiologically active polypeptide in cells of a blue-green alga by stably transforming the cells of a blue-green alga with a carrier DNA containing a structural gene encoding the polypeptide, characterized in that the carrier DNA is DNA which contains a structural gene encoding the physiologically active polypeptide, the transcription initiation region of the RuBisCO gene of *Anacystis nidulans* located upstream of the structural gene, and the transcription termination region of the RuBisCO gene located downstream of the structural gene.

The method for expression of this invention is described in more detail below.

[1] Creation of a carrier DNA

A specific method is as shown in the later described example for preparing a carrier DNA wherein a structural gene encoding a physiologically active polypeptide (hereinafter sometimes referred to as "useful structural gene" for convenience's sake) is ligated to the transcription initiation region, SD-like sequence and transcription termination region of the ribulose-1,5-diphosphoric acid carboxylase/oxygenase (RuBisCO) [refer to K. Shinozaki and M. Sugiura, Mol. Gen. Genet. 200:27–32(1985), Masanobu Kumano and Masahiro Sugiura, Iden (heredity) 38(12):26–31(1984), etc.].

(1) Preparation of the transcription initiation (promoter) region of RuBisCO

A DNA fragment containing the promoter of RuBisCO can be prepared by cutting it out from plasmid pANE18 (wherein is inserted an EcoRI fragment of about 5.6 MDa containing the RuBisCO promoter region in the EcoRI site of pBR322) disclosed for example in a literature of K. Shinozaki et al. [Proc. Natl. Acad. Sci. USA, 80:4050–4054 (1983)] with restriction endonucleases EcoRI, SacI, and PstI according to a conventional method (T. Maniatis et al., Molecular Cloning—A Laboratory Manual—published by Cold Spring Horbor Laboratory).

(2) Preparation of the transcription termination (terminator) region of RuBisCO

The terminator region of RuBisCO can be prepared by cutting it out from plasmid pANP1155 (wherein a PstI fragment of about 1.5 MDa is inserted containing the terminator region of RuBisCO in the PstI site of pBR322) disclosed in a literature of K. Shinozaki et al. [Proc. Natl. Acad. Sci. USA 80:4050–4054(1983)] using restriction endonucleases PstI and Eco52I.

(3) Preparation of the SD-like sequence

Into the recombinant DNA to be used in the invention, an SD-like sequence is introduced, as a ribosome recognition sequence, upstream of the useful structural gene and downstream of the promoter region.

Preferably used as the SD-like sequence is one complementary to the ribosomal RNA of a host blue-green alga, and a base sequence GGAG can be used as the SD-like sequence in case where *Anacystis nidulans* 6301 strain as a blue-green alga. However, the SD-like sequence is not limited thereto and other base sequences known as a SD-like sequence can likewise be used. Such SD-like sequences have a small base number and are, usually, prepared by synthesis.

Further, the SD-like sequence is usually located before ATG (translation initiation site) and the length (base number) from the SD-like sequence to ATG now possibly influence expression of the useful structural gene, and therefore, it is desirable to adjust the length in accordance with the kind of host, the base sequence of the structural gene, etc. so that the expression amount becomes optimum. The length varies depending on the kind of the host blue-green alga, the base sequence of the structural gene, etc. but is generally on the order of from 3 to 10 bases, and the optimum length can experimentally be determined in accordance with the base sequence of the structural gene of the host, etc.

Preparation of a DNA fragment containing the SD-like sequence can usually be carried out using a sequence before ATG (translation initiation site) or a sequence including ATG, and synthesis of the DNA fragment can easily be carried out according to gene manipulation any technique known per se [refer for example to "Zoku Seikagaku Jikken Koza 1 Idenshi Kenkyu Ho II" (Lectures of Biochemical Experiments 1 Methods for Studying Genes II) edited by Japan Society for Biochemistry and published by Tokyo kagaku Dojin Co., Ltd. (1987)].

(4) Preparation of the useful structural gene

Physiologically active polypeptides (hereinafter sometimes referred to as "useful peptide" for convenience's sake) capable of being expressed by the method of the invention are not limited to particular ones, and various useful peptides can efficiently be expressed according to the method of the invention.

Examples of useful peptides capable of being expressed by the method of the invention are SOD, (human, murine, etc.) interleukin, human-interferon-$\alpha$, -$\beta$, or -$\gamma$, human-insulin, human-tumor necrosis factor (TNF), human-colony-stimulating factor (CSF), human-tissue plasminogen activator (TPA), human-prourokinase, urokinase, human-blood coagulation factor (I–V, VII–XIII), human-erythropoietin, human-nerve growth factor, human-atrial natriuretic peptide ($\alpha$-hANP), human-pancreas-secretory trypsin inhibitor, (human, bovine, porcine, chicken, fish) growth hormone, growth hormone releasing factor, antibodies (immunoglobulins), insecticidal proteins (BT proteins, etc.), seed-stored proteins (phaseolin, zein, glutenin, glycinin, hordein, etc.), etc., and polypeptides having substantially the same amino acid sequence as these useful peptides have.

The polypeptide having substantially the same amino acid sequence as the useful peptide is used herein in a sense such that it includes the useful peptide itself as well as polypeptides analogous to the useful peptide wherein part of the amino acid sequence of the useful peptide is replaced by other amino acid(s) in a range such that the activities which the useful peptide inherently possesses are not substantially lost.

Therefore, if human-SOD used in the later example is taken as an example, "polypeptides having substantially the same amino acid sequence as human-SOD" include, besides hSOD polypeptides having the amino acid sequences reported by Jabusch et al., [Biochemistry, 19:2310–2316 (1980)] and reported by Barra et al. [FEBS Letters 120:53–55(1980)], polypeptides analogous to hSOD wherein part (generally 5 or less, preferably 2 or less) of the amino acid sequence is replace by other amino acid(s) in a range such that the enzymatic activities as hSOD are not substantially lost. Specific example thereof are (a) hSOD (b) a polypeptide wherein the sixth cystein residue (Cys) of hSOD is replaced by an alanine reside (Ala) (refer to Japanese Laid-Open Patent Publication No. 156884/1990)

(c) a polypeptide wherein the 111th cystein residue (Cys) of hSOD is replace by serine residue (Ser) (refer to Japanese Published Patent Publication No. 130684/1987)

(d) a polypeptide wherein the sixth cystein residue (Cys) is replaced by an alanine residue (Ala) and the 111th cystein residue (Cys) is replaced by a serine residue (Ser) (refer to Japanese Patent Publication No. 273473/1988).

Useful structural genes encoding such useful peptides as above can be prepared by extracting and cloning them from cells of supply sources such as animals, plants and microorganisms having an ability to produce a useful peptide or by chemical synthesis.

(5) Construction of an operon capable of being expressed containing a useful structural gene The thus prepared RuBisCO promoter region, SD-like sequence-containing DNA fragment and RuBisCO terminator region are, together with the physiologically active polypeptide-encoding useful structural gene, ligated in the order of (Promoter region)-(DNA fragment containing SD-like sequence)-(Translation initiation codon, ATG)-(Useful structural gene)-(Translation termination codon)-(Terminator region) according to a method known per se to create an operon capable of being expressed in cells of blue-green algae.

It is unnecessary that the numbers of the promoter and the SD-like sequence are one respectively, and it is also possible to use two or more promoters in a file and/or use two or more SD-like sequences in a file.

It is possible to transform a host with the above useful structure gene-containing operon in a state substantially as it is, depending on the kind of the host and/or operon, etc., but usually, the operon is first introduced into a vector (plasmid) suitable for the host and then used for transformation.

(6) Vector

Comprehensive kinds of vectors usable in cells of blue-green algae can be used as vectors into which the above operon capable of being expressed can be introduced. Examples of such vectors are pUC 104 and pUC 105 [C. J. Kuhlemeier et al., Mol. Gen. Genet. 184:249–254(1981)]; pLS103 [L. A. Sherman and P. van de Putte, J. Bacteriol, 150:410–413(1982)]; pDPL13 [S. Gendel et al., J. Bacteriol, 156:148–154(1983)]; pUC303 [C. J. Kuhlemeier et al., Plasmid 10:156–163(1983)]; pSG111 [S. S. Golden and L. A. Sherman, J. Bacteriol, 155:966–972 (1983)]; pPUC29 [C. J. Kuhlemeier et al., Gene 31:109–116(1984)]; pPLAN Bal [D. E. Landenbach et al. Mol. Gen. Genet, 199:300–305 (1985)]; pBAS18 [K. Shinozaki et al., Gene 19:221–223 (1982)], etc.

Further, such vectors can, if necessary, be derived from plasmids and viruses, and for example, shuttle vectors pBAX 18, pBAX 20, etc. capable of replicating in cells of *Escherichia coli* and blue-green algae can also be used advantageously, which were created by the present inventors using the OriA region of plamsid pBA1 derived from *Ancystis nidulans,* the multicloning region of plasmid pUC and the OriE region of the ColE1 plasmid of *Escherichia coli* (refer to the later-described example and the patent application which was filed on Mar. 8, 1991 by the present applicant and wherein the title of the invention is "Novel Plasmid" (Japanese Patent Application No. 67774/1991, corresponding to U.S. application Ser. No. 07/946,415 filed on Nov. 6, 1992, originally filed as International application PCT/JP92/00267 filed on Mar. 6, 1992).

(7) Construction of a carrier DNA

The operon stated in the above (5) which is capable of being expressed and contains a useful structural gene can be introduced into such a vector (plasmid) as stated in the above (6) according to gene manipulation techniques known per se.

For example, a hSOD operon DNA fragment prepared according to the description of the above (5) using a hSOD-encoding useful structural gene is combined with a DNA fragment obtained by cleaving, for example, the EcoRI recognition site of for example pBAS 18 or pBAX 18 replicable in cells of *Anacystis nidulans* with an endonuclease EcoRI, and $T_4$ DNA ligase is made to act thereon to obtain a hSOD-expressing vector into which the useful structural gene is introduced. It is unnecessary that the number of the operon to be inserted into the vector is one, and it is also possible to introduce 2, 3, 4 or more copies of the operon in a row provided that they are in the same direction.

The thus obtained hSOD-expressing vector can be cloned in *Escherichia coli* according to a conventional method (T. Maniatis et al., Molecular Cloning—A Laboratory Manual—Published by Cold Spring Horbor Laboratory).

[2] Transformation

The following can, for example, be mentioned as cells of blue-green algae which can be stably transformed using the thus created carrier DNA.

*Anacystis nidulans* 6301 (Synechococcus PCC 6301),
*Anacystis nidulans* R2 (Synechococcus PCC 7942),
Synechococcus PCC 7002,
Synechococcus PCC 7418 (*Aphanothece halophitica*),
Synechocystis PCC 6803,
Synechocystis PCC 6714,
*Spirulina platensis,*
Anabaena PCC 7120 (Nostoc PCC 7120),
Nostoc PCC 7119 (Anabaena PCC 7119),
Calothrix PCC 7601, etc.

Transformation of cells of these host blue-green algae with the above carrier DNA can be carried out by a method known per se, for example by R. D. Porter [CRC Critical Reviews in Microbiology 13(2):111–132], D. A. Lightfoot et al. [J. General, Microbiology 134:1509–1514(1988)], S. S. Golden et al. [J. Bacteriol, 158:36–42(1984)], H. Daniell et al. [Proc. Natl. Acad. Sci. USA 83:2546–2550(1986)], T. Matsunaga et al. [Appl. Biochem. Biotechnol. 24/25:151–160(1990)], etc.

For example, *Anacystis nidulans* can be transformed by introducing thereinto a hSOD expression vector according to the method of D. A. Lightfoot et al.

After selection of the resulting transformants based on ampicillin-resistance or the like, it is possible to confirm the obtainment of the desired transformant by the immunoblotting method, the Ouchterlony method, SOD activity staining in polyacylamide gel, measurement of SOD activity, etc.

It is possible to express the physiologically active polypeptide by culturing the thus obtained transformant under irradiation with light in a medium known per se and suitable for the proliferation of the host cells. Preferably, the medium contains a suitable amount of a drug such as ampicillin for selectively proliferating the transformant.

When the transformant host is *Anacystis nidulans,* suitable media are BG-11 medium, MDM medium, etc. and suitable culture temperature as a culture condition is generally 10° to 35° C., preferably 25° to 30° C. Further, suitable pH of the medium is usually in the range of 7 to 8 and suitable illuminance is in the range of 500 to 5,000 lux. Culture can be carried out under such conditions for the order of 5 to 20 days. Further, culture can be carried out under standing or stirring conditions.

According to the thus mentioned method of this invention, it is possible to obtain the useful peptide in a very high expression efficiency and separate and recover the useful peptide produced in the cells of the blue-green alga according to methods known per se. For example, the separation and recovery can be carried out by collecting the cells from the culture broth by centrifugation, and, after fracture, subjecting the resulting fractured cells to an appropriate combination of usually known operations such as, for example, salting out, dialysis, ion exchange chromatography, gel filtration chromatography, chromatofocusing, hydrophobic interaction chromatography, affinity chromatography and electrophoresis.

The thus prepared physiologically active polypeptides can be utilized as medicinal drugs, chemicals not included in medicinal drugs but used in medicinal treatment, cosmetics, etc.

Further, the transformed blue-green algae cultured under irradiation with light can be collected, after culture, by centrifugation, etc. and utilized as such as food, feed or functional food.

Further, the RuBisCO promoter used in the recombinant DNA in this invention can induce the expression in a large amount of the useful structural gene located downstream thereof under control of light, and thus the promoter has advantages, for example, that it is unnecessary to use an expensive drug usually used when expression is induced using the lac, tac or trp promoter of *Escherichia coli,* or the like.

BRIEF DESCRIPTION OF THE DRAWINGS

FIG. 6 is the creation drawing of hSOD operon.

FIG. 7 (pannels A and B) are the base sequence of hSOD operon (SOD7) (SEQ ID NO:2).

EXAMPLES

Figure 1:
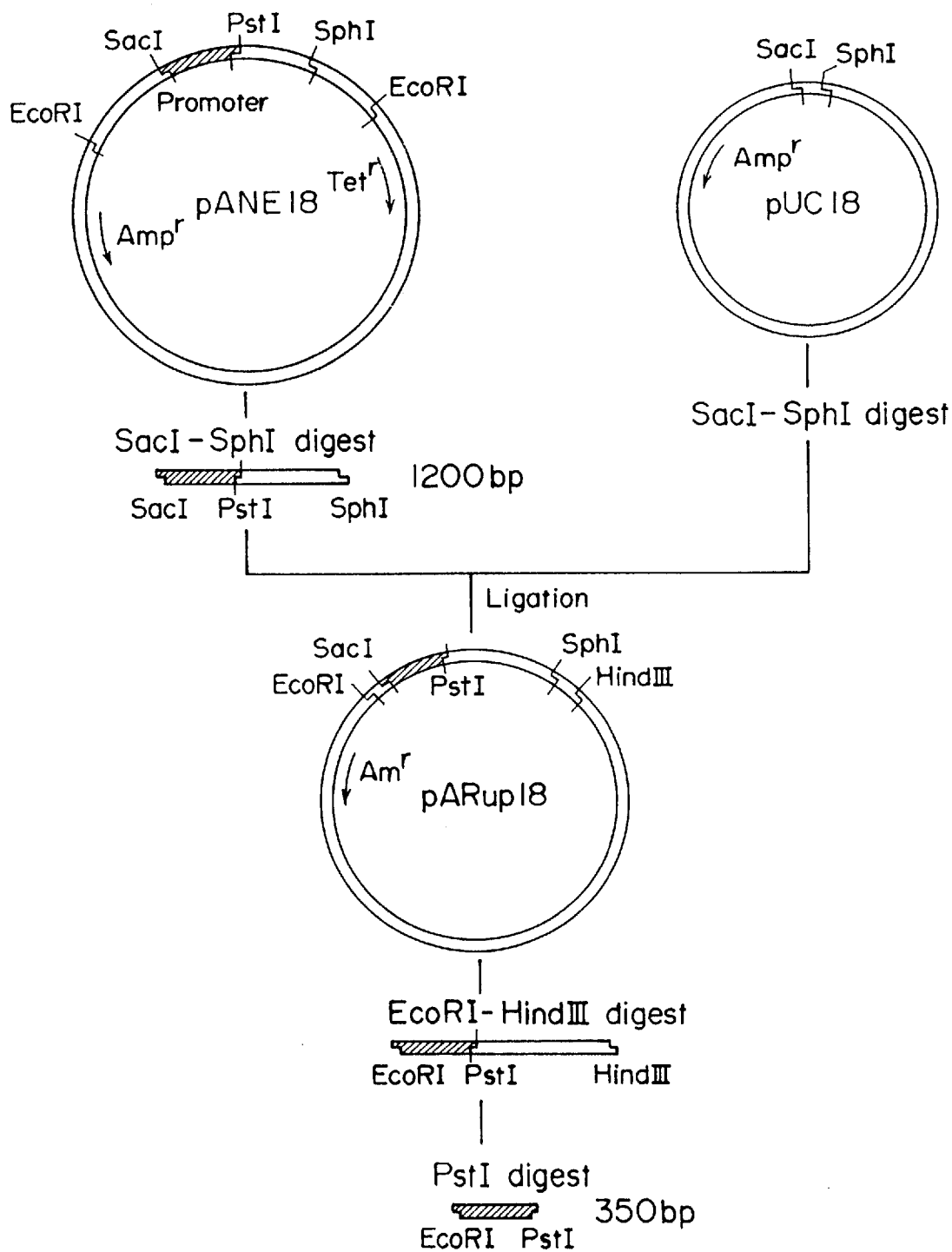
FIG. 1 is a process drawing for preparation of the *Anacystis nidulans* RuBisCO expression regulation region (EcoRI-PstI fragment).

This invention is more specifically described below by an example.

Example 1

I Preparation of an expression regulation region (I-1) Cloning of pANE 18

40 ng (1 μl) of pANE 18 (K. Shinozaki et al., Proc. Natl. Acad. Sci. USA 80:4050–4054(1983) wherein in the EcoRI site of pBR322 had been inserted a 5,600 bp fragment containing the promoter region of the ribulose-1,5-diphosphate carboxylase/oxygenase gene of the *Anacystis nidulans* 6301, was added to 100 μl of the cell suspension of the 50 mM Cells-treated *Escherchia coli* HB 101 strain, and the mixture was gently mixed. The mixture was incubated in ice water for 30 minutes and further incubated at 42° C. for 3 minutes to make the cells take the DNA therein. To this suspension was added 1 ml of LB medium (10 g/l bactotrypton, 5 g/l yeast extract, 10 g/l NaCl), and incubation was carried out with shaking at 37° c. for 1 hour. 100 μl and 200 μl of this cell suspension was taken and plated on an LB agar medium (containing 50 μg/ml ampicillin and 1.5% agar). This plate was incubated at 37° C. for 24 hours and then the resulting colonies were isolated.

The isolated colonies were inoculated with a platinum loop into 2 ml of a 2YT liquid medium (containing 16 g/l bactotraptone, 10 g/l yeast extract, 5 g/l NaCl and 50 μg/ml ampicillin) and cultured at 37° C. overnight. 1 ml of the culture was taken and added to 200 ml of a 2YT liquid medium (containing 100 μg/ml ampicillin) and culture was carried out at 37° C. overnight. The cultured cells were collected by centrifugation at 8,000 rpm for 10 minutes, and plasmid DNA was prepared therefrom in a large amount according to the SD-alkali method (B. Perbal, A. Practical Guide to Molecular Cloning, pages 273 to 276, Published from John Wiley and Sons Inc.).

(I-2) Isolation of the SacI-SphI fragment (refer to FIG. 1)

In an Eppendorf tube (volume 1.5 ml), sterilized water was added to 10 μl (10 μg) of pANE 18 DNA prepared in a large amount, 10 μl of 10×Low buffer (100 mM Tris-HCl (pH 7.5), 100 mM MgCl$_2$, 10 mM dithiothreitol (DTT)) and 50 units of SacI (produced by Takara Shuzo Co., Ltd.) to make the total volume 100 μl, and the mixture was subjected to reaction at 37° C. for 3 hours. After the reaction, 15 μl of 10×High buffer (500 mM Tris-HCl (pH 7.5), 100 mM MgCl$_2$, 10 mM DTT, 100 mM NaCl), 50 units of SphI (produced by Takara Shuzo Co., Ltd.) and 30 μl of sterilized water were added, and reaction was further carried out at 37° C. for 3 hours. After the reaction, 1/10 volume of 3M sodium acetate (pH 4.8) and 2.5 volumes of ethanol were added, and the mixture was left as it was at −20° C. for two or more hours. The formed precipitate was collected by centrifugation at 15,000 rpm and 4° C. for 10 minutes, washed with 70% ethanol and dried under reduced pressure. The residue was dissolved in 50 μl of TE (10 mM Tris-HCl (pH 8.0), 1 mM EDTA), a 1/10 volume of a marker for electrophoresis (0.25% Bromophenol Blue, 0.25% xylenecyanol, 30% glycerol) was added, the mixture was mounted on 1.5% agarose, and electrophoresis was carried out at 50 V for 1.5 hours using TAE buffer (40 mM Tris-acetate, 2 mM ETDA). After the electrophoresis, the gel was immersed in a 0.5 μg/ml ethidium bromide solution (in TAE) for 15 minutes to carry out staining of DNA. The stained gel was mounted on a transilluminator and irradiated with ultraviolet ray, and a band containing the desired DNA was cut out. The desired DNA fragment (about 1,200 bp). was purified using a DNA-purifying kit GENECLEAN (produced by BI0101 Co.).

(I-3) Cloning in pUC18 of the SacI-SphI fragment (1) SacI-SphI digestion of pUC 18

In an Eppendorf tube (volume 1.5 ml), sterized water was added to 10 μl (10 μg) of pUC 18 DNA, 5 μl of 10×Low buffer and 50 units of SacI to make the total volume 50 μl, and the mixture was subjected to reaction at 37° C. for 3 hours. After the reaction, 7.5 μl of 10×High buffer, 50 units of SphI and 37.5 μl of sterilized water were added, and reaction was further continued at 37° C. for 3 hours. Phenol:chloroform:isoamyl alcohol (25:24:1) was added in an equivolume to the reaction solution, and the mixture was intensely stirred and subjected to centrifugation at 15,000 rpm and 4° C. for 4 hours, and the water layer was taken. To this water layer were added a 1/10 volume of 3M sodium acetate (pH 4.8) and 2.5 volumes of ethanol to ethanol precipitate DNA. The precipitate was collected by centrifugation at 15,000 rpm and 4° C. for 10 minutes, washed with 70% ethanol and dried under reduced pressure. The residue was dissolved in 20 μl of TE and used in the following experiment.

(2) Insertion of the SacI-SphI fragment (1,200 bp) into pUC18 (SacI-SphI)

24 µl of Takara DNA ligation Kit A liquid (produced by Takara Shuzo Co., Ltd.) was added to 0.1 µg (2 µl) of the SacI-SphI fragment DNA and 0.5 µg (1 µl) of pUC 18 (SacI-SphI), followed by sufficient stirring. To this solution was added 3 µl of Takara DNA ligation Kit B liquid, the mixture was sufficiently stirred, and incubation was carried out at 160° C. for 1 hour. After the reaction, this solution was used for transformation of *E. coli* JM 109 cells.

(3) preparation in a large amount of pARup 18

To 5 µl (100 µg) of the ligation solution was added 100 µl of the cell suspension of the *E. coli* JM 109 treated with $CaCl_2$, followed by gentle mixing. The mixture was subjected to incubation in ice water for 30 minutes and then to incubation at 42° C. for 2 minutes to make the cells take the DNA therein. 1 ml of a 2YT liquid medium was added to this suspension, and incubation was carried out at 37° C. for 1 hour with shaking. 100 µl and 200 µl of this cell suspension was removed and plated on a 2YT agar medium (containing 50 µg/ml ampicillin, 40 mg/l 5-bromo-4-chloro-3-indolyl-β-D-thiogalactoside (X-gal), 23.83 mg/l isopropyl-β-D-thiogalactopyranoside (IPTG) and 1.5 % agar). This plate was incubated at 37° C. for 24 hours, and the obtained white colonies were spotted on a fresh 2YT agar medium (containing 50 µg/ml ampicillin, X-gal, IPTG and 1.5% agar) and cultured at 37° C. overnight to isolate a white colony.

The isolated white colony was inoculated with a platinum loop into 2 ml of a 2YT liquid medium (containing 50 µg/ml ampicillin) and cultured at 37° C. overnight. 1 ml of the culture was taken and transferred into a 1.5 ml Eppendorf tube, and centrifuged at 15,000 rpm for 30 seconds to collect the cells. The collected cells were suspended in 150 µl of a SET buffer (20% sucrose, 50 mM Tris-HCl (pH 7.6), 50 mM EDTA), 5 µl of an RNase solution (10 mg/ml ribonuclease A, 0.1M sodium acetate (pH 4.8), 0.3 mM EDTA) was added, and the mixture was sufficiently stirred by a voltex mixer. To this was added 350 µl of a lysing liquid (1% SDS, 0.2N NaOH), and the mixture was gently stirred by turning the tube upside down to complete lysing. The resulting lysed liquid was incubated in ice water for 10 minutes, 250 µl of 3M sodium acetate (pH 4.8) was added, and the mixture was sufficiently mixed and then left as it was in ice water for 30 minutes. This mixed liquid was centrifuged at 15,000 rpm and 4° C. for 10 minutes to precipitate the SD and chromosome DNA. The supernatant was transferred into another Eppendorf tube, an equal amount of isopropyl alcohol was added, and the mixture was sufficiently mixed and then centrifuged at 15,000 rpm and 4° C. for 7 minutes, and plasmid DNA was collected as precipitate. The precipitate was dissolved in sterilized water, and part of the solution was subjected to restriction endonuclease EcoRI and Hind III (both are produced by Takara Shuzo Co., Ltd.) digestion. The digest was subjected to 1.5% agarose gel electrophoresis to confirm that the SacI-SphI fragment of 1,200 bp was inserted in pUC18.

The colony about which it was confirmed that the SacI-SphI fragment was inserted in pUC18 was transferred into 400 ml of a 2YT liquid medium (containing 100 µg/ml ampicillin) and cultured overnight. The cultured cells were collected by centrifugation at 8,000 rpm at 40° C. for 10 minutes and the plamsid DNA was prepared in a large amount by the SDS-alkali method.

(I-4) Isolation of the EcoRI-PstI fragment (refer to FIG. 1)

(1) Isolation of the EcoRI-Hind III fragment

In an Eppendorf tube (volume 1.5 ml), sterilized water was added to 10 µl (10 µg) of the pARup 18 DNA solution prepared in a large amount, 20 µl of 10×K buffer (200 mM Tris-HCl (pH 8.5), 100 mM $MgCl_2$, 100 mM DTT, 1,000 mM KCl) and 40 units of Hind III to make the total volume 200 µl. 20 Eppendorf tubes in total were prepared containing the same contents as above, and reaction was carried out at 37° C. for 3 hours. After the reaction, the mixture was treated with phenol-chloroform, and DNAs were collected by ethanol precipitation and dissolved in 155 µl of sterilized water. To this solution were added 40 µl of 5×EcoRI buffer (500 mM Tris-HCl (pH 7.5), 35 mM $MgCl_2$, 250 mM NaCl, 35 mM 2-mercaptoethanol, 0.05 % bovine serum albumin (BSA)) and 40 units of EcoRI to make the total volume 200 µl. Reactions were carried out at 37° C. for 3 hours. After the reaction, the reaction mixture was likewise subjected to phenol-chloroform treatment and ethanol precipitation to recover DNAs. The desired DNA fragment (about 1,200 bp) was separated by 1.5% agarose gel electrophoresis and purified using a DNA-purifying kit GENECLEAN.

(2) Isolation of the EcoRI-PstI fragment (about 350 bp)

To 40 µg (86 µl) of the purified DNA fragment were added 10 µl of 10×High buffer and 48 units of PstI (produced by Takara Shuzo Co., Ltd.) in an Eppendorf tube (volume 1.5 ml) to make the total volume 100 µl, and reaction was carried out at 37° C. for 3 hours. After the reaction, 1.5% agarose gel electrophoresis was carried out to separate the desired DNA fragment (about 350 bp). The DNA was electrically eluted from the gel and purified using a nucleic acid-purifying cartridge NENSORB 20 (produced by Dupont Co.)

Figure 2:
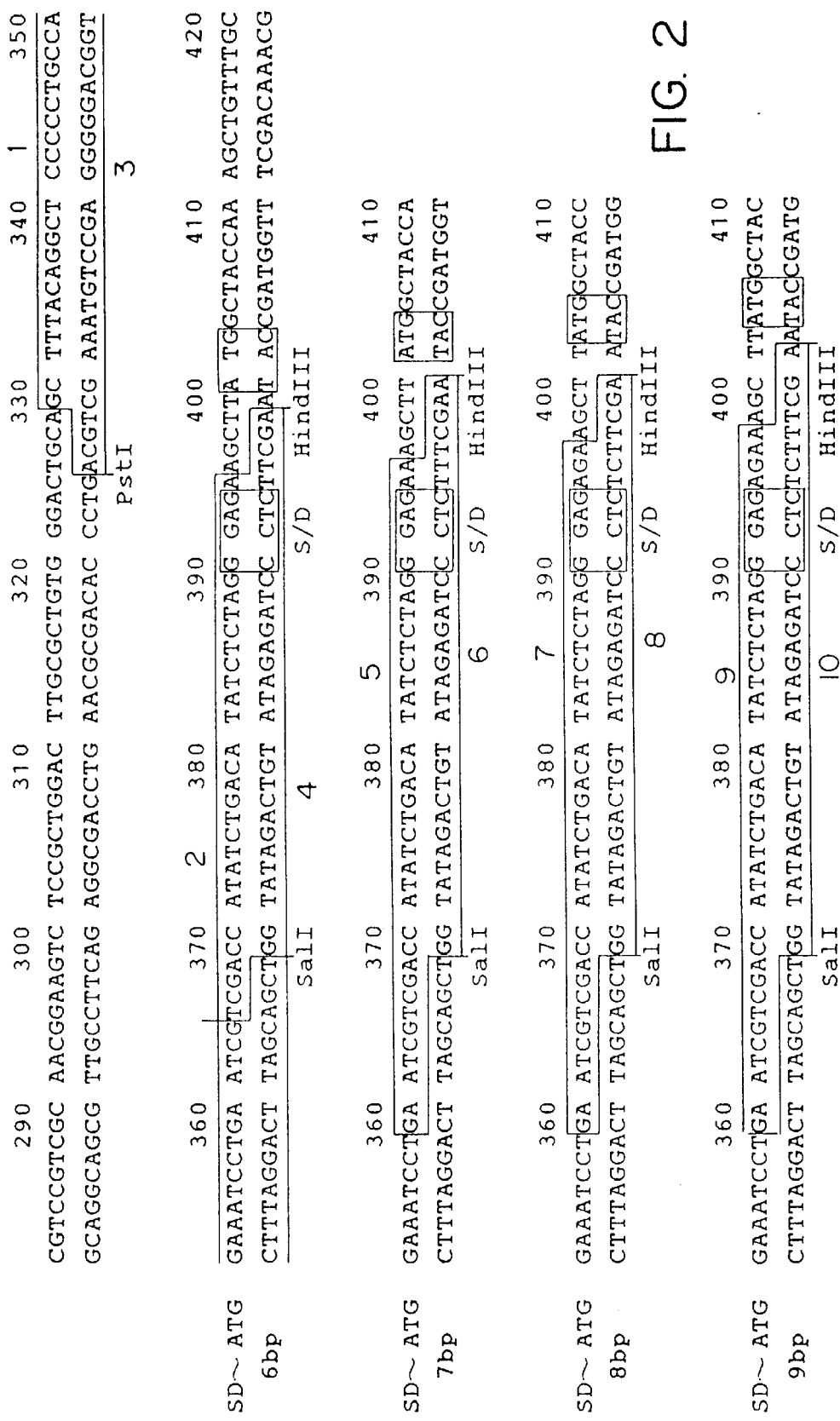
FIG. 2 is the base sequence of CO oligonucleotides chemically synthesized for synthesis of the SD-like sequence-containing region (PstI-Hind III fragment) (SEQ ID NO:1).

(I-5) Synthesis of a PstI-Hind III fragment (1) Synthesis and purification of oligonucleotides For the purpose of synthesis of an expression regulation region containing the Shine Dalgarno (S/D) sequence, 10 oligonucleotides (refer to FIG. 2) were synthesized by the phosphoamidite method using a DNA synthesizer 380 A (produced by Applied Biosystems Japan Co.). 2 ml in total of ammonium water (27% or more) was added to the silica gel column after completion of the synthesis in a way of addition of 0.5 ml portions and every 15 minutes, and each oligonucleotide was cut out from the silica support and collected in a vial. 1 ml of ammonia water was further added to this vial, and the vial was sealed by a cap and parafilm, or the like and heated at 55° C. for 8 or more hours to remove the protective group (acyl group) at the base part. The vial was taken out from the constant temperature bath and brought back to room temperature, and after removed of the cap the contents were concentrated to dryness under reduced pressure. After the drying, the residue was dissolved in 200 µl of a 0.01M triethylamine-acetic acid solution (TEAA, pH 7.5), and then subjected to HPLC using a AM-313-ODS (produced by Yamamura Kagaku Kenkyusho Co., Ltd.) and elution with acetonitrile and concentration gradient of 0.1M TEAA and the main peak was taken from the eluate in fractions. The obtained peak was concentrated to dryness under reduced pressure, 100 µl of 80% acetic acid (acetonitrile solution) was added, and the mixture was mixed and then left as it was at room temperature for 30 minutes to remove the dimethyltrityl (DMTr) group at the $5^1$-terminus and convert it to an OH group. 30 minutes thereafter,the mixture was rapidly concentrated to dryness, the residue was dissolved in 200 µl of 0.01M TEAA (pH 7.5), an equal volume of diethyl ether was added, and the DMTr group was removed by the extraction. The resulting solution was concentrated to dryness under reduced pressure, the residue was dissolved in 110 µl of 0.01M TEAA (pH 7.5) and purified again by preparative HPLC. The eluate fractions containing the oligonucleotide were concentrated to dryness under reduced pressure, and the residue was dissolved in TE and used in the following experiment.

(2) Phosphorylation of the synthesized oligonucleotides with Kinase

4 μg of each of the purified oligonucleotides was mixed with 120 μl portions of a kinase buffer (50 mM Tris-HCl (pH 7.6), 10 mM MgCl$_2$, 0.1 mM EDTA, 5 mM DTT, 0.1 mM spermidine, 1.7 μM ATP) respectively, 9 units of T$_4$ polynucleotide kinase (produced by Takara Shuzo Co., Ltd.) was added, and incubation was carried out at 37° C. for 15 minutes. Then ATP was added to the final concentration of 1 mM, 9 units of T$_4$ polynucleotide kinase was added again, and incubation was carried out at 37° C. for 25 minutes. After the reaction, the mixture was subjected to heat treatment of 90° C for 5 minutes to inactivate the enzyme. Phosphorylated oligonucleotides were purified using nucleic acid-purifying cartridges NENSORB 20.

(3) Preparation of PstI-Hind III fragments

Figure 3:
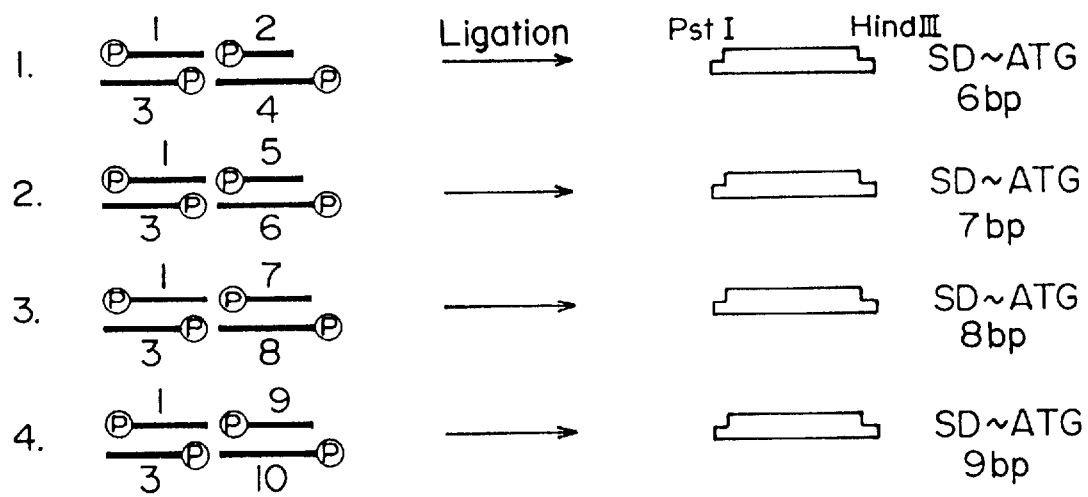
FIG. 3 is a process drawing for preparation of the SD-like sequence-containing region (PstI-Hind III fragment).

4 PstI-Hind III fragments having a different base number with one another were prepared by direct ligation of the oligonucleotides with T$_4$ DNA ligase (refer to FIG. 3). 20 μl of a 5×ligation buffer (250 mM Tris-HCl (pH 7.6), 10 mM MgCl$_2$) and sterilized water were added to 1.5 μg of the oligonucleotide located at the 5'-terminus of the strand of the lower tier among the oligonucleotides constituting each PstI-Hind III fragment and 1 μg each of the other oligonucleotides to make the total volume 80 μl. The resulting solution was heated at 90° C. for 5 minutes and gradually cooled up to 4° C. over a period of 2 hours, 10 μl each of 100 mM DTT and 10 mM ATP were added, 2.5 units of T$_4$ ligase (produced by Takara Shuzo Co., Ltd.) was added and incubation was carried out at 40C for 15 hours. The reaction solution was treated with an equal volume of phenol-chloroform, and DNA was recovered by ethanol precipitation and used in the following experiment.

Figure 4:
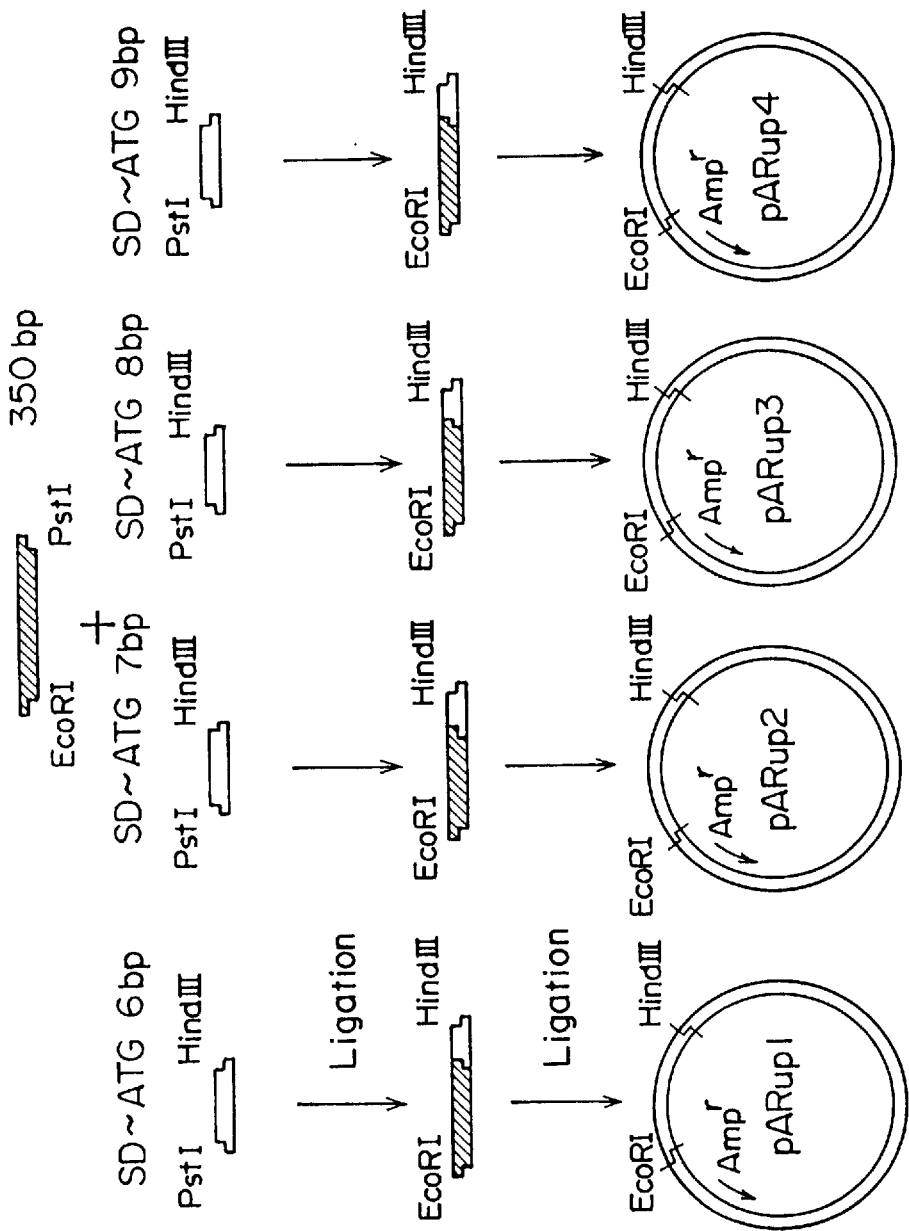
FIG. 4 is a process drawing for preparation of the RuBisCO expression regulation region (EcoRI-Hind III fragment).

(I-6) Preparation of EcoRI-Hind III fragments (refer to FIG. 4)

(1) Direct ligation of the EcoRI-PstI fragment (promoter region) and each PstI-Hind III fragment 1.0 μg portions of the EcoRI-PstI fragment isolated in the above (I-4) and 0.5 μg each of the four PstI-Hind III fragments having a different base number with one another were mixed with 5 μl portions of 0.3M NaCl, respectively. 5 μl of Takara ligation kit B liquid was added to each of the resulting solutions and incubation was carried out at 26° C. for 1 or more hours. After the reaction, the solution was treated with phenol-chloroform and subjected to ethanol precipitation in a conventional manner to recover DNA.

(2) Digestion of the ligation reaction mixtures with Hind III-EcoRI

Each of the recovered DNA residues was dissolved in 14.5 μl portions of sterilized water respectively. 4 μl of a 5×Hind III buffer (50 mM Tris-HCl (pH 7.5), 35 mM MgCl$_2$, 300 mM NaCl) and 12 units (1.5 μl) of Hind III were added to each solution, and reaction was carried out at 37° C. for 1.5 hours. After the reaction, 4 μl of the 5×EcoRI buffer, 12 units (1.0 μl) of EcoRI and 5 μl of sterilized water were further added, and reaction was carried out at 37° C. for 1.5 hours. The reaction solution was treated with an equal amount of phenol-chloroform and then DNA was recovered by ethanol precipitation.

(I-7) Cloning of the four expression regulation region EcoRI-Hind III fragments having a different base number from one another (refer to FIG. 4)

(1) EcoRI-Hind III digestion of pUC18

In an Eppendorf tube (volume 1.5 ml), sterilized water was added to 25 μg of pUC18, 10 μl of a 10×K buffer (200 mM Tris-HCl (pH 8.5), 100 mM MgCl 10 mM DTT, 100 mM KCl) and 64 units (8 μl) of Hind III to make the total volume 100 μl, and reaction was carried out at 37° C. for 3 hours. This reaction solution was treated with an equal volume of phenol-chloroform and DNA was recovered by ethanol precipitation. The DNA residue was dissolved in 75 μl of sterilized water, 20 μl of 5×EcoRI buffer and 60 units (5 μl) of EcoRI were added, and reaction was carried out at 37° C. for 3 hours. After the reaction, the reaction mixture was likewise subjected to phenol-chloroform treatment and ethanol precipitation. The recovered DNA was dissolved in TE to 0.25 μg/μl and used in the following experiment.

(2) Insertion of the four expression regulation region EcoRI-Hind III fragments into pUC18 (EcoRI-Hind III)

60 ng (1 μl) each of the four EcoRI-Hind III fragments and 500 ng (2 μl) portions of the pUC18 (EcoRI-Hind III) were put in Eppendorf tubes, respectively, and 24 μl portions of Takara ligation kit A liquid were added, followed by sufficient mixing. Further, 3 μl portions of Takara ligation kit B liquid were added to these mixed solutions, and after mixing reaction was carried at 16° C. for 2 or more hours. These solutions were used in the following experiment.

(3) Preparation of pARup 1, 2, 3 and 4 in a large amount

To 3 μl (56 ng) each of the ligation solutions were added 100 μl portions of a cell suspension of E. coli JM 109 treated with CaCl$_2$, followed by gentle mixing. The mixed solutions were subjected to incubation in ice water for 30 minutes and further incubated at 42° C. for 2 minutes to make the cells take DNA therein. To these suspensions were added 1 ml portions of 2YT liquid medium, and after shaking each culture at 37° C. for 1 hour the mixtures were plated on 2YT agar medium (containing 50 μg/ml ampicillin, 40 mg/l X-gal, 23.83 mg/l IPTG and 1.5% agar). By preparing plasmids from the obtained white colonies and analyzing restriction endonuclease maps, colonies were screened carrying the desired plasmids pARup 1, 2, 3 and 4, respectively.

The respective colonies carrying plasmid pARup 1, 2, 3 and 4 were culture in 200 ml portions of 2YT liquid medium (containing 100 μg/ml ampicillin) and the respective plasmid DNAs were prepared in a large amount by the SDS-alkali method.

(I-8) Isolation of the EcoRI-Hind III fragments

20 μg (20 μl) each of the plasmid DNAs (pARup 1, 2, 3 and 4) prepared in a large amount were put in Eppendorf tubes respectively, and 20 μl portions of 10×K buffer, 120 units (15 μl) portions of Hind III and sterilized water were added thereto to make the total volume 200 μl. Such Eppendorf tubes were prepared in a number of 6 per each plasmid. Incubation was carried out at 37° C. for 3 hours. After the reaction, the reaction mixtures were phenol-chloroform treated, and DNAs were collected by ethanol precipitation and dissolved in 150 μl portions of sterilized water. To these DNA solutions were added 40 μl portions of 5×EcoRI buffer and 120 units (10 μl) portions of EcoRI were added, and incubation was carried out at 37° C. for 3 hours. After the reaction, DNAs were recovered by ethanol precipitation. The desired respective DNA fragments were separated by 1.5% agarose gel electrophoresis. DNAs were electrically eluted from the gels respectively, and purified using a nucleic acid-purifying cartridge NENSORB 20 (ARup 1, 2, 3 and 4).

Figure 5:
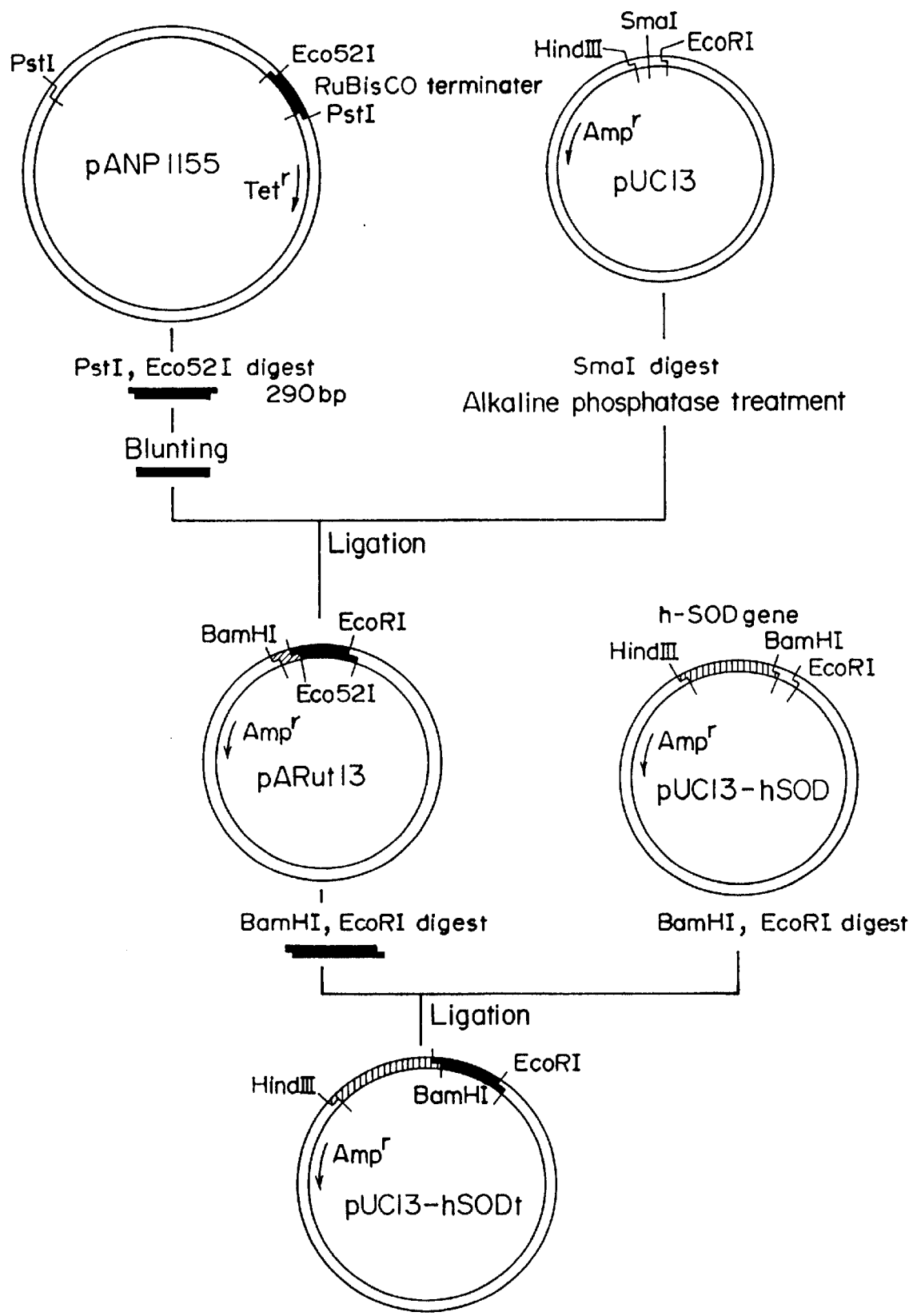
FIG. 5 is a drawing showing preparation of the RuBisCO transcription termination region and construction of pUC-hSODt plasmid.

II Preparation of a transcription termination (terminator) region (refer to FIG. 5)

(II-1) Cloning of pANP1155

To 100 μl of a cell suspension of E. coli JM 109 treated with 50 mM CaCl$_2$ was added 500 ng (0.5 μl) of pANP 1155 (K. Shinozaki et al., Proc. Natl. Acad. Sci. USA 80:4050–4054(1983)) wherein in the PstI site of pBR322 was inserted a fragment of about 1500 bp containing the terminator region of the ribulose-1,5-diphosphate carboxylase/oxygenase gene of Anacystis nidulans 6301, followed by gentle stirring. The mixed liquid was subjected to incubation in ice water for 30 minutes and further to incubation at 42° C. for 2 minutes to make the cells take DNA therein. To this suspension was added 1 ml of an LB liquid medium, and after shaking culture at 37° c. for 1 hour, the mixture was plated on an LB agar medium (containing: 12.5 µg/ml tetracycline and 1.5% agar), and the resulting colonies were isolated.

The isolated colonies were cultured in 2.8 liters of a 2YT liquid medium (containing 25 µg/ml tetra-cycline), and the plasmid DNA was prepared in a large amount by the SDS-alkali method.

(II-2) Preparation of a Eco52I-PstI fragment
(1) Isolation of a PstI fragment

In an Eppendorf tube (volume 1.5 ml), sterilized water was added to 20 µg (20 µl) of pANP1155 DNA prepared in a large amount, 20 µl of 10×High buffer and 120 units (10 µl) of PstI to make the total volume 200 µl. Eppendorf tubes (volume 1.5 ml) containing the same contents as above were prepared in a total number of 6, and incubation was carried out at 37° C. for 3 hours in each tube. After the reaction, DNAs were recovered by ethanol precipitation and then the desired DNA fragment (about 1,500 bp) was separated by 1.5% agarose gel electrophoresis. The separated DNA was purified using GENECLEAN and used in the following experiment.

(2) Eco52I digestion of the PstI fragment

To 64.5 µl (about 10 µg) of the PstI fragment DNA solution were added 7.5 µl of a 10×Eco52I buffer (100 mM Tris-HCl (pH 9.0), 30 mM MgCl$_2$, 1,000 mM NaCl, 0.1% BSA) and 18 units (3 µl) of Eco52I (produced by Toyobo Co., Ltd.), and incubation was carried out at 37° C. for 3 hours. After the incubation, the mixture was subjected to phenol-chloroform treatment and ethanol precipitation and the precipitated DNA was recovered. The recovered DNA was dissolved in 8 µl of sterilized water.

(II-3) Creation of pARutl3
(1) Blunting of the Eco52I-PstI fragment

1 µl of DNA Blunting Kit (produced by Takara Shuzo Co., Ltd.) 10×buffer was added to 8 µl of the DNA solution of the Eco52I-PstI fragment prepared in II-2, and after incubation at 70° C. for 5 minutes, the mixture was transferred into a constant temperature bath of 37° C. To this solution was added 1 µl of T$_4$ DNA polymerase, and the mixture was gently mixed by pipetting and subjected to reaction at 37° C. for 5 minutes. After the reaction, to this solution was added 40 µl of the DNA dilution buffer supplied in DNA Blunting Kit, and the mixture was intensely stirred by vortex to inactivate the enzyme.

(2) SmaI digestion of pUC13 and dephosphorylation

To 20 µg (20 µl) of pUC13 DNA were added 40 µl of a 5×SmaI buffer (50 mM Tris-HCl (pH 8.0), 35 mM MgCl$_2$, 100 mM KCl, 35 mM 2-mercaptoethanol, 0.05 % BSA), 80 units (10 µl) of SmaI (produced by Takara Shuzo Co., Ltd.) and 130 µl of sterilized water, followed by reaction at 30° C. for 4 hours. After the reaction, the reaction mixture was treated with phenol-chloroform and subjected to ethanol precipitation, and DNA was recovered. The recovered DNA was dissolved in 100 µl of 0.1M Tris-HCl (pH 8.0), 10 µl of an alkaline phosphatase solution (1.0 unit of alkaline phosphatase (AP, produced by Takara Shuzo Co., Ltd.), 10 mM Tris-HCl (pH 7.5), 50 mM NaCl, 1 mM ZnSO$_4$) was added, and reaction was carried out at 37° C. for 2 hours. After the reaction, another 10 µl of the alkaline phosphatase solution was added, followed by incubation at 65° C. for 30 minutes. The reaction solution was treated with phenol-chloroform and DNA was precipitated with ethanol, collected and dissolved in TE to 0.5 µg/µl.

(3) Insertion of the blunted fragment into pUC13 (SmaI, AP)

32 µl of Takara ligation Kit A liquid was added to 2 µl (about 100 ng) of the blunted fragment DNA solution and 2 µl (1.0 µg) of a solution of the alkaline phosphatase-treated pUC13 DNA, followed by sufficient stirring. To this solution was added 4 µl of Takara ligation Kit B liquid, and after sufficient stirring incubation was carried out at 16° C. for one or more hours. After the reaction, this solution was used for transformation of E. coli JM 109.

(II-4) Preparation of a BamHI-EcoRI fragment
(1) Preparation of pARut13 in a large amount To 1 µl (about 40 ng) of the ligation solution was added 100 µl of a cell suspension of E. coli JM 109 treated with 50 mM CaCl$_2$, followed by gentle mixing. The mixed solution was subjected to incubation in ice water for 30 minutes and then to incubation at 42° C., for 2 minutes to make the cells take DNA therein. 1 ml of a 2YT liquid medium was added to this suspension, and after shaking at 37° C. for 1 hour the suspension was plated on a 2YT agar medium (containing 50 µg/ml ampicillin, 40 mg/l X-gal, 23.83 mg/l IPTG and 1.5% agar). Plasmids were prepared from the obtained white colonies, their restriction endonuclease maps were analyzed and thereby a colony was screened carrying the desired plasmid pARut 13. The screened colony was cultured in 400 ml of a 2YT liquid medium (containing 100 µg/ml ampicillin), and a large amount of the plasmid DNA was prepared by the SDS-alkali method.

(2) Isolation of a BamHI-EcoRI fragment

8 Eppendorf tubes (volume 1.5 ml) were prepared in each of which to 15 µg (15 µl) of the plasmid DNA (pARut 13) prepared in a large amount were added 20 µl of a 10×K buffer, 120 units (10 µl) of BamHI (produced by Takara Shuzo Co., Ltd.) and sterilized water to make the total volume 200 µl. These tubes were subjected to incubation at 30° C. for 3 hours. After the reaction, the reaction mixtures were treated with phenol-chloroform, and DNAs were collected by ethanol precipitation and dissolved in 110 µl portions of sterilized water, respectively. To these DNA solutions were added 30 µl portions of 5×EcoRI buffer and: 120 units (10 µl) portions of EcoRI, followed by incubation at 37° C. for 3 hours. After the reaction, DNAs were recovered by ethanol precipitation, and the desired DNA fragments (about 300 bp) were separated by 1.5% agarose gel electrophoresis. The DNAs were electrically eluted from the gels, and purified using nucleic acid-purifying cartridges NENSORB 20.

III Creation of an h operon
(III-1) Ligation of the transcription termination region to h gene
(1) BamHI-EcoRI digestion of PUC13-h-SOD In an Eppendorf tube, to 10 µg (20 µl) of pUC13-h-SOD (refer to Example 1 of the specification of Japanese Patent Application No. 210129/1989) wherein in the Hind III-BamHI site of pUC13 had been inserted a DNA fragment of full strand length (475 bp) encoding human superoxide dismutase were added 40 µl of 5×EcoRI buffer, 120 units (10 µl) of EcoRI and sterilized water to make the total volume 200 µl, and incubation was carried out at 37° C. for 3 hours. After the reaction, the reaction mixture was treated with phenol-chloroform, and DNA was collected by ethanol precipitation and dissolved in 215 µl of sterilized water. To this solution were added 25 µl of 10×K buffer and 100 units (10 µl) of BamHI, and reaction was carried out at 30° C. for 3 hours. After the reaction, DNA was purified using GENECLEAN.

(2) Insertion of the transcription termination region (BamHI-EcoRI) into pUC13-h-SOD (BamHI-EcoRI)

11.2 µl of Takara ligation kit A liquid was added to 500 ng (1 µl) of pUC13-h-SOD (BamHI-EcoRI) DNA and 60 ng (0.4 µl) of the transcription termination region prepared in II, following by sufficient mixing. 1.4 µl of Takara ligation kit B liquid was added to this solution, and after sufficient stirring incubation was carried out at 16° C. for 30 minutes. After the reaction, this solution was used for transformation of E. coli JM 109.

(III-2) Preparation of a Hind III-EcoRI (hSOD-terminator) fragment (1) Preparation of pUC13-hSODt in a large amount To 2 µl (about 70 ng) of the ligation solution was added 100 µl of a cell suspension of E. coli JM 109 treated with 50 mM $CaCl_2$, followed by gentle mixing. This mixed solution was subjected to incubation in ice water for 30 minutes and then to incubation at 42° C. for 2 minutes to make the cells take DNA therein. After addition of 1 ml of a 2YT liquid medium, the resulting mixture was subjected to shaking culture at 37° C. for 1 hour and then plated on a 2YT agar medium (containing 50 µg/ml ampicillin, 40 mg/l X-gal, 23.83 mg/l IPTG and 1.5% agar). Plasmids were prepared from the resulting white colonies, and a colony carrying the desired DNA fragment was screened by analysis of its restriction endonuclease maps. The screened colony was culture in 60 ml of a 2 YT liquid medium (containing 100 µg/ml ampicillin) and plasmid DNA was prepared by the SDS-alkali method.

(2) Isolation of the HindII-EcoRI fragment

Two Eppendorf tubes (volume 1.5 ml) were prepared in each of which to 50 µl (25 µg) of the prepared PUC13-hSODt DNA solution were added 20 µl of 10×K buffer, 120 units (15 µl) of Hind III and sterilized water to make the total volume 200 µl. In each tube incubation was carried out at 37° C. for 3 hours. After the reaction, the reaction mixtures were treated with phenol-chloroform, and DNAs were collected by ethanol precipitation and dissolved in 150 µl portions of sterilized water. To these DNA solutions were added 40 µl portions of 5×EcoRI buffer and 120 units (10 µl) of EcoRI, and incubation was carried out at 37° C. for 3 hours. After the reaction, DNAs were recovered by ethanol precipitation, and the desired DNA fragment (about 790 bp) was separated by 1.5% agarose gel electrophoresis. The DNA was purified by GENECLEAN.

(III-3) Ligation of the Hind III-EcoRI (hSOD-terminator) fragment to the expression regulation region ARup 1, 2, 3 and 4 (refer to FIG. 6)

Eppendorf tubes were prepared wherein to 1.12 µg (2.1 µl) each of the expression regulation regions (ARup 1, 2, 3 and 4) and 2.11 µg (2.2 µl) portions of the Hind III-EcoRI fragment were added 4 µl portions of a 5×ligation buffer (250 mM Tris-HCl (pH 7.6), 50 mM $MgCl_2$), 2 µl portions of 100 mM DTT, 2 µl portions of ATP, 2.5 units (1 µl) portions-of $T_4$ DNA ligase (produced by Takara Shuzo Co., Ltd.) and sterilized water to make the total volume 20 µl, respectively. In these tubes incubation was carried out at 15° C. overnight, and the reaction was stopped by a thermal treatment at 60° C. for 10 minutes. To these solutions were added 10 µl portions of 5×EcoRI buffer, 12 units (1 µl) portions of EcoRI and sterilized water were added respectively to make the total volume 50 µl. These solutions were subjected to incubation at 37° C. for 3 hours. After the reaction, the desired respective DNA fragments (refer to FIG. 7, each about 1200 bp) were separated by 2 % agarose gel electrophoresis and purified using Geneclean.

(III-4) Cloning of the four hSOD gene-expressing DNA fragments (1) EcoRI digestion of pUC18 and subsequent alkaline phosphatase treatment In an Eppendorf, to 20 µg (30 µl) of plasmid pUC18 DNA were added 40 µl of a 5×EcoRI buffer, 120 units (10 µl) of EcoRI and sterilized water were added to make the total volume 200 µl, and incubation was carried out at 37° C. for 3 hours. After the reaction, the reaction mixture was treated with phenol-chloroform, and DNA was collected by ethanol precipitation and dissolved in 100 µl of 0.1M Tris-HCl (pH 8.0). 10 µl of the alkaline phosphatase solution was added to this solution and incubation was carried out at 37° C. for 1 hour. After the reaction, another 10 µl of the alkaline phosphatase solution was added and incubation was carried out at 65° C. for 30 minutes. The reaction solution was treated with phenol-chloroform, and DNA was collected by ethanol precipitation and dissolved in TE to 0.16 µg/µl.

(2) Insertion of the hSOD operon fragments into pUC18 (EcoRI and AP-treated)

24 µl portions of Takara ligation kit A liquid were added to 100 ng (1 µl) each of hSOD operon (Promoter-SOD-terminators 1, 2, 3 and 4) DNAs and 320 ng (2 µl) portions of the EcoRI and alkaline phosphatase-treated pUC18 DNA, respectively, followed by sufficient stirring. 3 µl portions of Takara ligation kit B liquid were added to these solutions, and after sufficient stirring incubation was carried out at 1° C. overnight.

(3) Preparation of pUC18-Rupt-hSOD 1, 2, 3 and 4 in a a large amount

To 4 µl (about 50 ng) each of the ligation solutions were added 200 µl portions of a cell suspension of E. coli JM 109 strain treated with 50 mM $CaCl_2$, followed by gentle mixing. These mixed liquids were subjected to incubation in ice water for 30 minutes and further to incubation at 42° C. for 2 minutes to make the cells take DNA therein. 1 ml portions of a 2YT liquid medium were added to these suspensions, and after shaking at 37° C. for 1 hour, the mixture were plated on portions of a 2YT agar medium (containing 50 µg/ml ampicillin, 40 mg/ml X-gal, 23.83 mg/l IPTG and 1.5% agar). Plasmids were prepared from the obtained white colonies, and by analyzing their restriction endonuclease maps colonies carrying the desired respective plasmids (pUC18-Rupt-hSOD 1, 2, 3 and 4), were screened. Each of the screened colonies was cultured in 200 ml portions of a 2YT liquid medium (containing 100 µg/ml ampicillin), and each plasmid DNA was prepared by the SDS-alkali method in a large amount.

(4) Isolation of EcoRI fragments (about 1200 bp)

Eppendorf tubes were prepared in a number of 3 per each plasmid into which tubes 40 µl portions of 5×EcoRI buffer, 120 units (10 µl) portions of EcoRI and 130 µl portions of sterilized water were added to about 20 µg (20 µl) each of the plasmids (pUC18-Rupt-hSOD 1, 2, 3 and 4) prepared in a large amount. In these tubes incubation was carried out at 37° C. for 3 hours. After the reaction, DNAs were collected by ethanol precipitation and dissolved in 100 µl portions of TE about each plasmid. The desired respective DNA fragments (about 1,200 bp) were separated by 1.5% agarose gel electrophoresis and purified using GENECLEAN.

Figure 8:
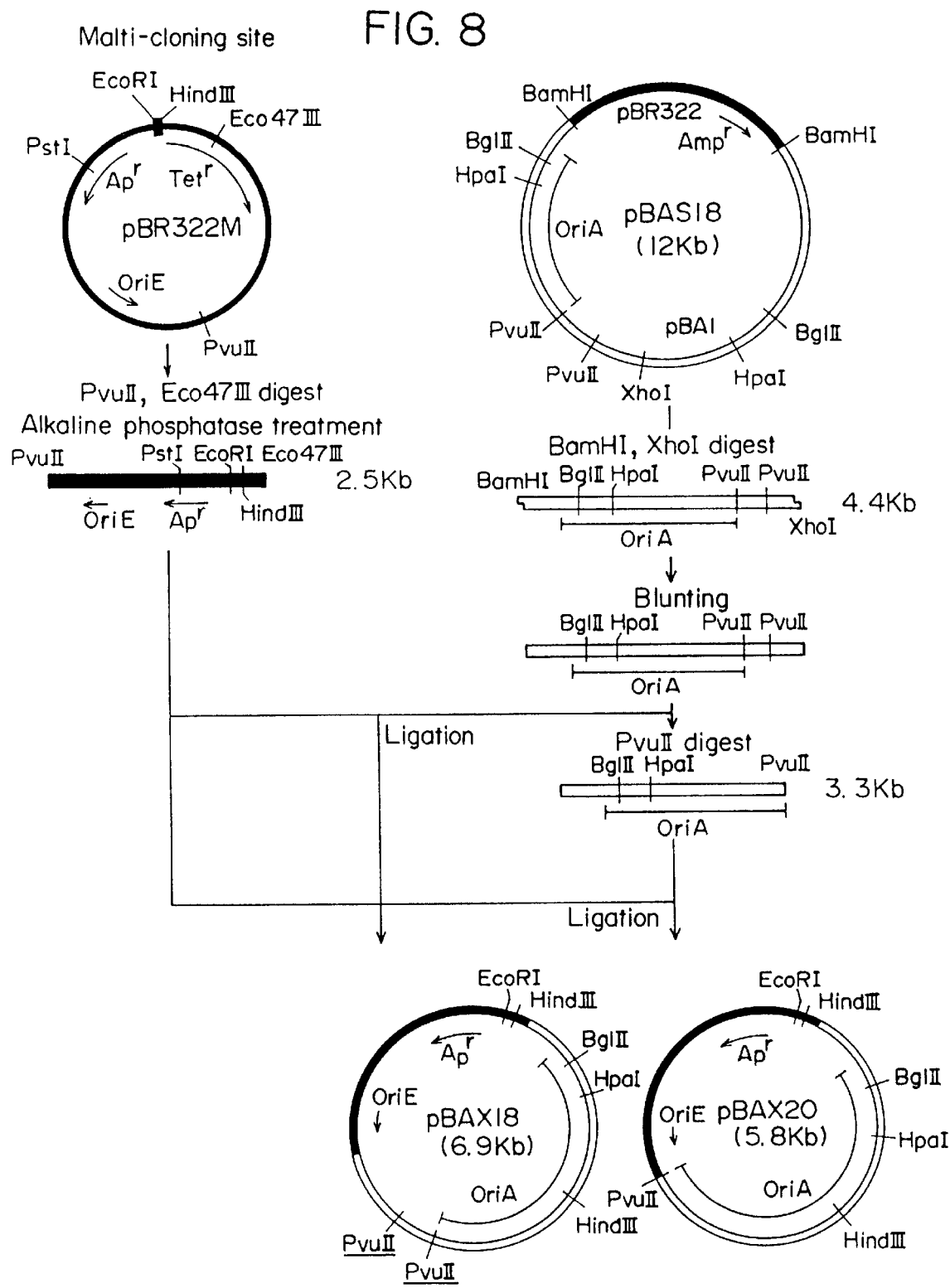
FIG. 8 is the construction drawing of vector plasmids pBAX 18 and 20.

IV Creation of an hSOD gene expression vector for blue-green algae (refer to FIG. 8)

(IV-1) Introduction of a multicloning site (derived from pUC18 into pBR322

(1) EcoRI-Hind III digestion of pBR322 and subsequent alkaline phosphatase treatment To 20 µl (10 µg) of a pBR 322 DNA solution were added 40 µl of 5×Hind III buffer (50 mM Tris-HCl (pH 7.5), 35 mM MgCl$_2$, 300 mM NaCl), 80 units (10 µl) of Hind III and 130 µl of sterilized water, and incubation was carried out at 37° C. for 2 hours. After the reaction, to this solution were added 40 µl of 5×EcoRI buffer, 120 units (10 µl) of EcoRI and 50 µl of sterilized water, and reaction was further carried out at 37° C. for 2 hours. After the reaction, the reaction mixture was treated with phenol-chloroform, and DNA was collected by ethanol precipitation and dissolved in 100 µl of 0.1M Tris-HCl (pH 8.0). 10 µl of the alkaline phosphatase solution was added to this solution, and incubation was carried out at 37° C. for 1 hour. After the reaction, 10 µl of the alkaline phosphatase solution was added, and incubation was carried out at 65° c. for 30 minutes. This solution was treated with phenol-chloroform and DNA was recovered by ethanol precipitation.

(2) Isolation of a multicloning site (EcoRI-Hind III) from pUC18

Two Eppendorf tubes were prepared in each of which 20 µl of 10×K buffer, 80 units (10 µl) of Hind III and 140 µl of sterilized water were added to 30 µl (20 µg) of the pUC18 DNA solution, and incubation was carried out at 37° C. for 3 hours. After the reaction, the reaction mixture were treated with phenol-chloroform, and each DNA was collected by ethanol precipitation and dissolved in 112.5 µl of sterilized water. To these solutions were added 30 µl portions of 5×EcoRI buffer and 90 units (7.5 µl) portions of EcoRI, respectively, and incubation was carried out at 37° C. for 3 hours. DNA was collected by ethanol precipitation and then subjected to 1.5 % agarose gel electrophoresis to separate the desired DNA fragment (about 50 bp). The DNA was electrically eluted from the gel and purified by phenol-chloroform treatment and ethanol precipitation.

(3) Ligation of pBR322 (EcoRI-Hind III digestion) to the multicloning site

1 µl of TE and 24 µl of Takara ligation kit A liquid were added to 0.2 µg (1 µl) of pBR322 (EcoRI-Hind III, AP treatement) DNA and 0.2 µg (1 µl) of the multi-cloning site DNA, followed by sufficient stirring. 3 µl of Takara ligation kit B liquid was added to this solution, and reaction was carried out at 16° C. for 4 hours.

(4) Cloning of plasmid pBR322M

To 3 µl (40 ng) of the ligation solution was added 200 µl of a cell suspension of E. coli HB 101 treated with CaCl$_2$, followed by gentle mixing. This mixed liquid was subjected to incubation in ice water for 30 minutes and then to incubation at 42° C. for 2 minutes to make the cells take DNA therein. 1.8 ml of a 2YT liquid medium was added to this suspension, and after shaking culture at 37° C. for 1 hour the mixture was plated on an LB agar medium (containing 50 µg/ml ampicillin). By preparing plasmids from the obtained colonies and analyzing their restriction endonuclease maps a colony carrying the desired plasmid (pBR 322M) was screened. The screened colony was cultured in 200 ml of a 2YT liquid medium (containing 100 µg/ml ampicillin), and plasmid DNA was prepared by the SDS-alkali method in a large amount.

(IV-2) Isolation of a PvuII Eco47III fragment (2550 bp)

Three Eppendorf tubes were prepared into each of which 10 µg (10 µl) of BR322M plasmid DNA prepared in the above (IV-1), 20 µl of 10×M buffer (100 mM Tris-HCl (pH 7.5), 10 mM MgCl$_2$, 10 mM DTT, 500 mM NaCl), 120 units (10 µl) of PvuII (produced by Takara Shuzo Co., Ltd.) and sterilized water were added to make the total volume 200 µl.

In these tubes incubation was carried out at 37° C. for 3 hours. After the reaction, the reaction mixtures were treated with phenol-chloroform, and DNAs were collected by ethanol precipitation and dissolved in 174 µl portions of sterilized water. To these solutions were added 20 µl portions of 10×H buffer and 24 units portions of Eco47III (produced by Takara Shuzo Co., ltd.), and incubation was carried out at 37° C. for 3 hours. DNAs were precipitated with ethanol and recovered, and the desired DNA fragment (2550 bp) was separated by 1.5% agarose gel electrophresis. The separated DNA fragment was purified using GENECLEAN and dissolved in 50 µl of 0.1M Tris-HCl (pH 8.0). 5 µl of alkaline phosphatase solution was added to this solution, and incubation was carried out at 37° C. for 1 hour. After the reaction, 5 µl of alkaline phosphatase solution was added, and incubation was further continued at 65° c. for 30 minutes. After the reaction, the reaction mixture was treated with phenol-chloroform, and DNA was collected by ethanol precipitation and dissolved in 20 µl of TE.

(IV-3) Separation of the replication initiation point in A. nidulans of pBAS18

Into E. coli HB 101 was introduced a shuttle vector pBAS18 (K. Shinozaki et al., Gene. 19:221–224 (1982)) between E. coli and A. nidulans wherein an endogenous plasmid (digested with pBA1 and BamHI) of A. nidulans 6301 had been inserted into the BamHI site of pBR322. The resulting strain was cultured in an LB liquid medium (containing 50 µg/ml ampicillin), and the vector was prepared in a large amount by the SDS-alkali method.

Three Eppendorf tubes were prepared into each of which 14 µg (20 µl) of the prepared pBAS18 DNA, 20 µl of 10×K buffer, 100 units (10 µl) of BamHI and sterilized water were added to make the total volume 200 µl, and incubation was carried out at 30° C for 3 hours. After the reaction, DNAs were recovered by ethanol precipitation, and the desired DNA fragment (pBA1, about 8.0 kbp) was separated by 1% agarose gel electrophoresis and purified using GENECLEAN.

To 2 µg (5 µl) of the separated and purified pBA1 (digested with BamHI) DNA were added 5 µl of 10×K buffer, 24 units (2 µl) of XhoI and 38 µl of sterilized water, and incubation was carried out at 37° C. for 3 hours. After the reaction, the reaction mixture was treated with phenol-chloroform and DNA was collected by ethanol preparation. Both termini of the obtained BamHI-XhoI-digested DNA were blunted using Takara ligation kit.

(IV-4) Creation of a miniaturized E. coli-A.nidulans shuttle vector pBAX18 (6.9 kbp)

(1) preparation of pBAX 18 (about 6.9 kb)

48 µl of Takara ligation kit A liquid was added to 40 ng (2 µl) of the blunted DNA and 200 ng (4 µl ) of the PvuII-Eco47III fragment DNA, and after sufficient stirring, 6 µl of B liquid was added and incubation was carried out at 16° C. for 4 hours. E. coli HB 101 strain was transferred using this solution and plated on an LB agar medium (containing 50 µg/ml ampicillin and 1.5% agar) to obtain colonies. Plasmids were prepared from the obtained colonies, and by analyzing their restriction endonuclease maps was screened a colony carrying the desired plasmid pBAX18. The screened colony was cultured in a 2YT liquid medium (containing 100 µg/ml ampicillin), and plasmid DNA was prepared by the SDS-alakali method.

(2) Preparation of pBAX20 (about 5.8 kb)

2 µl of 10×M buffer, 1 µl (12 units) of PvuII and 13 µl of sterilized water were added to 1 µg (4 µl) of the BamHI-XhoI (blunted) DNA fragment prepared in the above (IV-3), and incubation was carried out at 37° C. for 3 hours. To 2 µl (100 ng) of this reaction solution were added 100 ng (2 μl) of the PvuII-Eco47 DNA fragment prepared in (2) and 16 μl of Takara ligation kit A liquid, and after sufficient stirring, 4 μl of B liquid and incubation was carried out at 16° C. for 2 hours. After the reaction, E. coli HB 101 was transformed using this solution and plated on an LB agar medium (containing 50 μg/ml ampicillin and 1.5% agar) to obtain colonies. A colony carrying the desired plasmid (pBAX20) was screened from the obtained colonies and cultured in 200 ml of a 2YT liquid medium (containing 100 μg/ml ampicillin), and the plasmid DNA was prepared by the SDS-alkali method.

(IV-5) Cloning of a hSOD gene-expressing vector (1) EcoRI digestion of pBAX18 and subsequent alkaline phosphatase (AP) treatment Two Eppendorf tubes were prepared in each of which to 10 μg (20 μl) of pBAX 18 DNA were added 40 μl of 5×EcoRI buffer, 120 units (10 μl) of EcoRI and 130 μl of sterilized water to make the total volume 200 μl. In each tube, incubation was carried out at 37° C. for 3 hours, and DNA was purified by GENECLEAN and dissolved in 100 μl of 0.1M Tris-HCl (pH 8.0). 10 μl of the alkaline phosphatase solution was added to this solution, incubation was carried out at 37° C. for 1 hour, and after addition of another 10 μl of the alkaline phosphatase solution incubation was carried out at 65° C. for 30 minutes. After the reaction, the reaction mixture was treated with phenol-chloroform and DNA was recovered by ethanol precipitation.

(2) Ligation of the hSOD operon to pBAX18 (EcoRI, AP treatment), large amount preparation 0.5 μg (1 μl) portions of pBAX18 treated with EcoRI and AP were added to 0.25 μg (1 μl) each of the four hSOD operons (about 1.2 kbp) prepared in the above (III-4), respectively, and ligation was carried out using Takara ligation kit. E. coli HB 101 strains were transformed separately using these ligation solution, and the respective transformant-containing liquids were plated on LB agar media (containing 50 μg/ml ampicillin) to obtain colonies. Plasmids were prepared from the obtained colonies, and by analyzing their restriction endonuclease maps were screened colonies carrying the desired respective plasmids (pBAXSOD6, pBAXSOD7, pBAXSOD8, pBAXSOD9, pBAXSOD6-4, pBAXSOD7-4 and pBAXSOD8-4). The screened respective colonies were cultured in 50 ml portions of an LB liquid medium (containing 100 μg/ml ampicillin), and plasmid DNAs were prepared by the SDS-alkali method.

(3) EcoRI digestion of pBAS18 and subsequent alkaline phosphatase (AP) treatment In an Eppendorf tube, to 18 μg (30 μl) of pBAS18 DNA were added 40 μl of 5×EcoRI buffer, 12 units (10 μl) and 120 μl of sterilized water to make the total volume 200 μl, and incubation was carried out at 37° C. for 3 hours. After the reaction, the reaction mixture was treated with phenol-chloroform and then with chloroform, and DNA was recovered by ethanol precipitation. The recovered DNA was dissolved in 100 μl of 0.1M Tris-HCl (pH 8.0), 10 μl of an alkaline phosphatase solution (1 unit/10 μl) was added, and incubation was carried out at 37° C. for 1 hours. Thereafter, 10 μl of the alkaline phosphatase solution was added, and incubation was carried out at 65° C. for 30 minutes. After the reaction, the reaction mixture was treated with phenol-chloroform and then chloroform, and DNA was purified and recovered by ethanol precipitation.

(4) Ligation of the hSOD operons to pBAS18 (treated with EcoRI and AP) and large amount preparation 1.5 μg (2 μl) portions of the EcoRI and AP-treated pBAS18 were added to 0.25 μg (1 μl) each of the four hSOD operons (about 1.2 kb) prepared in the above (III-4), and ligation was carried out using Takara ligation kit. E. coli HB 101 strains were transformed using these reaction solutions, respectively, and plated on LB agar media (containing 50 μg/ml ampicillin—1.5% agar) to obtain colonies. Plasmids were prepared from the obtained colonies, an by analyzing their restriction endonuclease maps were screened colonies carrying the desired plasmids (pBASOD6, pBASOD7, pBASOD8 and pBASOD9). The screened respective colonies were cultured in 200 ml portions of a 2YT liquid medium (containing 100 μg/ml ampicillin), and plasmid DNAs were prepared using the SDS-alkali method.

V Expression of the hSOD gene using a blue-green alga Anacystis nidulans 6301 and R2

(V-1) Transformation of A. nidulans 6301 (Synechococcus PCC 6301) and R2 (Synechococcus PCC 7942)

The respective cells which had been cultured in 100 ml portions of a BG-11 liquid medium for 1 to 5 days were collected by centrifugation at 8,000 rpm for 5 minutes, and suspended in 10 ml portions of a fresh liquid medium ($10^8$–$10^9$ cells/ml). 1 ml portions of each of these cell suspensions were poured into polyethylene tubes (Falcon 2059), and the prepared plasmid DNA was put in concentrations of 0.1 to 10 μg in the tubes, respectively. The resulting tubes were covered with sheets of aluminum foil, respectively, and after culture at 30° C. overnight, the sheets of aluminum foil were removed, and then culture was continued at 30° C. for further 6 hours under irradiation with light (light source: a cool white fluorescent lamp; 1,000–2,000 lux). 100 to 500 μl each of these cell suspensions were taken and plated on BG-11 agar media (containing 1 mM sodium thiosulfate, 1 to 5 μg/ml ampicillin and 1.5% agar). These plates were cultured for 4 to 10 days under irradiation with light (light source: a cool white fluorescent lamp; 2,000–3,000 lux).

(V-2) Culture

The thus obtained colonies were transferred to 2 ml portions of a BG-11 liquid medium (containing 10 μg/ml ampicillin) and cultured for 10 days under irradiation with light (light source: a cool white fluorescent lamp; 2,000 to 3,000 lux). Then, these cultures were transferred to 100 ml portions of a BG-11 liquid medium (containing 10 μg/ml ampicillin), respectively, and cultured for 20 days under irradiation with light (2,000–3,000 lux). 10 ml each of these cultures were taken, transferred to 100 ml portions of a BG-11 liquid medium (containing 50 μg/ml ampicillin), respectively, and cultured for 20 days under irradiation with light. The respective cells were collected by centrifugation at 8,000 rpm and 4° C. for 10 minutes, resuspended in 1 mM Hepes buffers (pH 7.0), and washed by centrifugation. After washing, the respective cells were stored at −20° C. until the time of use in experiments.

(V-2) Detection of hSOD (1) h-SOD activity staining

Figure 9:
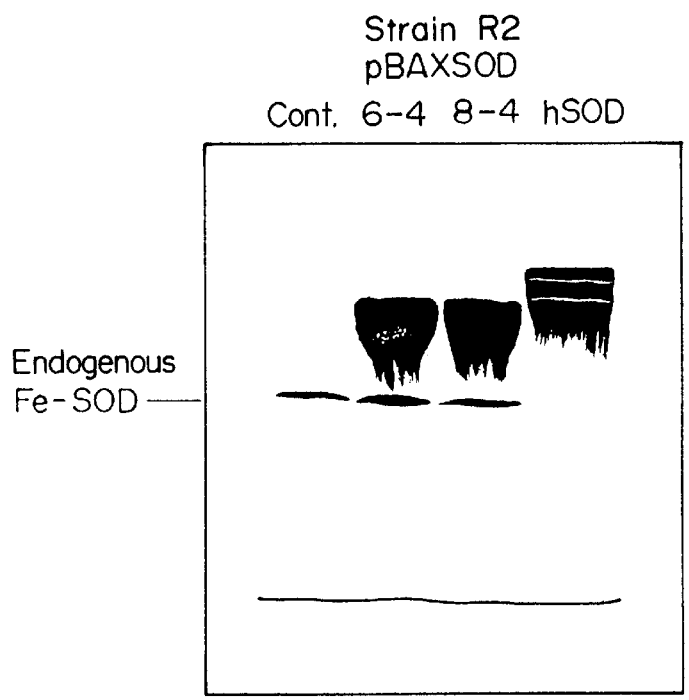
FIG. 9 is a drawing showing the result of the activity staining of SOD.

Electrophoresis was carried out using acryl-amide gel prepared by a photopolymarization method using riboflavin [Tanpakushitsu kakusan Koso (Protein, Nucleic Acid and Enzyme) 11:744(1966)]. After the electrophoresis, the gel was washed two to three times (5 minutes) with 50 mM potassium phosphate (pH 7.8)—0.5 mM EDTA, and then immersed for 7 minutes in a nitrobluetetrazolium (NBT) solution (2.5 mM NBT, 50 mM potassium phosphate, 0.5 mM EDTA, pH 7.8). Then, the gel was immersed in a riboflavin solution (100 μM riboflavin, 30 mM tetramethylethylenediamine, 50 mM potassium phosphate, 0.5 mM EDTA, pH 7.8), and stained in white light until there arose contrast in the gel. The results are shown in FIG. 9. In this drawing, the part having SOD activity is not stained and the other parts are stained purple. As is seen therefrom, hSOD activity was detected, besides the Fe-SOD activity which Anacystis nidulans itself possessed, in the transformants.

(2) Detection with an anti-human-SOD antibody
(2-1) Western blotting

Electrophoresis was carried out in a reducing state and under the conditions of Laemmli et al. (Nature 237, 680 (1970)) using 20% SDS-polyacrylamide gel. After the electrophoresis, the proteins in the gel were electrically transferred onto a nitrocellulose membrane (produced by Amasham Co., Hybond (C)). This membrane was immersed for 20 minutes in 50% methanol containing 0.3% $H_2O_2$ to inactivate endogenous peroxidase, and then immersed at 37° C. for 2 hours TBS (20 mM Tris-HCl, 0.9% NaCl, pH 7.4) containing 5% skim milk and 0.1% Tween 20 (blocking). The membrane subjected to the blocking treatment was washed for 5 minutes with a washing liquid (TBS containing 0.05% Tween 20) and then incubated at 37° C. for 2 hours in TBS containing $\frac{1}{1000}$ anti-human-SOD antibody (caprine IgG, produced by Binding Site Co.) and 0.1% Tween 20. The membrane was washed with the washing liquid for 20 minutes (5 minutes×5) and then stained with 40 ml of 0.1 M Tris-HCl (pH 7.4) containing 10 mg diaminobenzidine (DAB) and 15 μl of 32 % $H_2O_2$.

Figure 10:
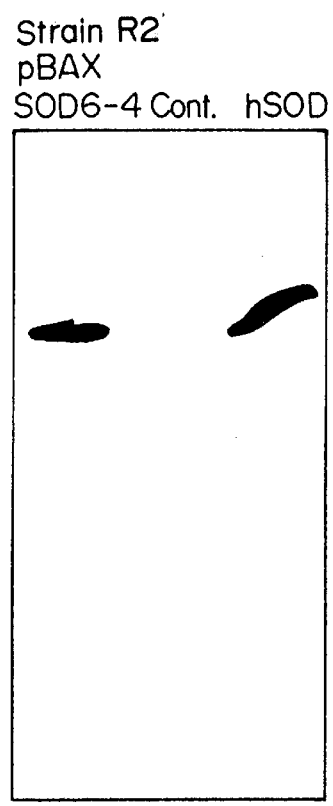
FIG. 10 is a drawing showing the result of Western blotting.

As a result, a band stained brown was detected in the lane where the extract from the transformant had been electrophoresed and at the same position as in a standard sample hSOD (produced by Sigma Co.) (FIG. 10).

(2-2) Ouchterlony method [Menekigaku Jikken Nyumon (A Guide to Immunological Experiments) pages 74 to 77, published by Gakkai Shuppan Center]

Figure 11:
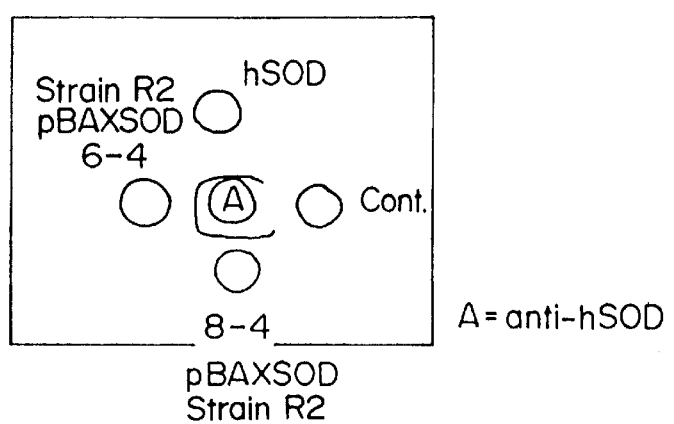
FIG. 11 is a drawing showing the result of Ouchterlony.

A 1.2% agarose solution (containing 10 mM phosphate buffer (pH 7.2), 0.15M NaCl and 0.1% $NaN_3$) was solidified to a thickness of 2 to 3 mm in a Petri dish (Falcon 1029), and holes were made at suitable positions. 10 μl of anti-human-SOD antibody was put in the center hole, and the extracts (10 μl each) of the transformants, the extract (40 μl) of A. nidulans R2 (non-transformant) as a control and a standard sample hSOD were put in the surrounding holes, respectively, and incubation was carried out at 4° C. overnight. After incubation, the agar plate was taken out from the Petri dish, and immersed in PBS (10 mM phosphate buffer, pH 7.2, 0.15 NaCl) and thereby sufficiently freed from proteins (PBS was replaced several times, 2 to 3 days). This plate was immersed in a 0.5% amide black solution (90 ml methanol, 10 ml glacial acetic acid) to stain it. As a result, it was revealed that a precipitation line was formed between the anti-human-SOD antibody and the standard sample hSOD, and between the anti-human-SOD antibody and the extracts (6-4, 8-4) of the transformants. Further, the precipitation lines appeared so that they combine to make a single line (a shape of ]), and thereby it was confirmed that antigens (human-SOD) identical to the standard sample hSOD were produced in the transformants (FIG. 11).

(3) Detection of an h-SOD activity

Although Anacystis nidulans has an endogenous SOD (Fe-SOD), it is possible to measure the activity of hSOD (Cu Zn-SOD) in distinction from that of the endogenous SOD (Fe-SOD) utilizing the difference in inhibition of them by 1 mM KCN. In an optical cell (for 1 ml) are put 50 mM potassium phosphate (pH 7.8), 0.1 mM EDTA, 0.1 mM xanthine, 10 μM cytochrome C (equine heart Type III, produced by Sigma Co.) and a sample (SOD), and the whole volume and made to be 980 μl. 20 μl of xanthine oxidase (produced by Boehringer-Mannheim Co.) was added thereto to initiate reaction, and cytochrome C reduction was determined as the initial rate (30 to 60 seconds) of increase of absorbance at 550 nm, and this value is expressed as γ. Cytochrome C reduction rate when no SOD sample is added is expressed as v. SOD inhibiting 50% cytochrome C reduction under these conditions is supposed to be ⅓ unit, and total unit number in the sample was determined from (v/γ-1) (Shokubutsu Koso Tanpakushitsu Kenkyu HO (Plant Enzyme Protein-Studying Methods) page 373, Koji Asada, published by Kyoritsu Publisher Co., Ltd.). Further, 100 mM KCl (10 μl) was added to the reaction solution on which γ had been measured, and cytochrome C reduction rate γ' and unit number were determined (v/γ'-1). The activity of hSOD {(v/γ-1)-(v/γ'-1)} formed in the cells of Anactystis nidulans was determined.

As a result, the specific activities (activity per 1 $A_{280}$ unit) of the crude extracts obtained from the transformants showed high values of 0.7 to 12 units/$A_{280}$ (Table 1).

TABLE 1

| Original vector plasmid | Expression vector | hSOD expression amount (specific activity, units/$A_{280}$) |
|---|---|---|
| pBAS18 | pBASOD6 | 6.57 |
|  | pBASOD7 | 8.85 |
|  | pBASOD8 | 7.61 |
|  | pBASOD9 | 5.98 |
| pBAX18 | pBAXSOD6 | 7.18 |
|  | pBAXSOD7 | 9.98 |
|  | pBAXSOD8 | 11.79 |
|  | pBAXSOD9 | 6.78 |

Further, these specific activities are strongly influenced by the kind of original vectors and the base number between the SD-like sequence and ATG, and pBAXSOD8 (base number between SD and ATG was 8 bases as determined from PBAX18) had the highest specific activity.

Industrial Applicability

According to the described present invention, it is possible to express useful peptides in an extremely high efficiency using cells of blue-green algae as hosts, and the prepared useful peptides can be utilized as medicinal drugs, chemicals not included in medicinal drugs but used in medical treatment, cosmetics, etc., and the cultured transformed blue-green algae can be utilizied as food, feed and/or functional food.

We claim:

1. A method for expressing a physiologically active polypeptide having enzymatic activity, therapeutic activity or both, in cells of a blue-green alga comprising the steps of (1) stably transforming the cells of said blue-green alga with a vector DNA which is a vector plasmid selected from the group consisting of plasmid PBAS18, plasmid pBAX18, and plasmid pBAX20, said vector DNA containing a structural gene encoding the physiologically active polypeptide, operably linked to at least one promoter region comprising the transcription initiation region of the RuBisCO gene of *Anacystis nidulans* located upstream of the structural gene, and the transcription termination region of the RuBisCO gene located downstream of the structural gene and (2) culturing said transformed cells under conditions that induce the expression of the structural gene encoding the physiologically active polypeptide.

2. A human-SOD-expressing vector comprising vector plasmid pBAS18, pBAX18 or pBAX20 into which a human-SOD operon comprising a human-SOD structural gene encoding a polypeptide having substantially the same amino acid sequence as human SOD, at least one promoter region comprising the transcription initiation region of the RuBisCO gene of *Anacystis nidulans* located upstream of the human-SOD structural gene, and the transcription termination region of the RuBisCO gene located downstream of the human-SOD structural gene is ligated.

3. The method of claim 1 wherein the vector plasmid is plasmid pBAS18, or plasmid pBAX18.

4. The method of carrier 1 wherein the physiologically active polypeptide is human SOD.

5. The human-SOD expressing vector of claim 2 wherein the vector plasmid is pBAS18 or PBAX18.

6. Cells of a blue-green alga transformed with the human-SOD-expressing vector of claim 2.

7. A process for preparing human-SOD which comprises culturing cells of the blue-green alga of claim 6 in a liquid medium under conditions that induce the expression of the human-SOD structural gene from the culture.

8. A method for preparing a physiologically active polypeptide having enzymatic activity, therapeutic activity or both which comprises (1) stably transforming blue-green algae cells with a vector DNA capable of expressing the polypeptide, said vector DNA comprising vector plasmid pBAS18, pBAX18 or pBAX20 having ligated therein an operon comprising a structural gene encoding said polypeptide, operatively linked to at least one promoter region comprising the transcription initiation region of the *Anacystis nidulans* RuBisCO gene located upstream of said structural gene, and the transcription termination region of the RuBisCO gene located downstream of said structural gene;

(2) culturing the resulting transformants in a liquid culture medium in the presence of white light and (3) recovering physiologically active polypeptide from the cell culture.

9. The method according to claim 8 wherein during culturing the illumination from the white light is in the range of from 500 to 5,000 lux.

10. The method according to claim 8 which further comprises collecting the transformants by centrifugation.

11. The method according to claim 8 which further comprises collecting the transformants and subjecting the collected transformants to lysis prior to recovering the physiologically active polypeptide.

12. The method according to claim 8 wherein the physiologically active polypeptide is human-SOD.

13. The method according to claim 1 wherein the vector DNA further comprises a Shine-Delgarno-like sequence operably linked upstream of the transcription initiation region of the RuBisCO gene.

14. The method according to claim 13 wherein the distance between the Shine-Delgarno-like sequence and the transcription initiation region of the RuBisCO gene is in the range of from 3 to 10 bases.

15. The human-SOD expressing vector according to claim 2 wherein the vector DNA further comprises a Shine-Delgarno-like sequence operably linked upstream of the transcription initiating region.

16. The human-SOD operon according to claim 15 wherein the distance between the Shine-Delgarno-like sequence and the transcription initiation region is in the range of from 3 to 10 bases.

17. The human-SOD expressing vector according to claim 2 wherein the vector DNA further comprises a Shine-Delgarno-like sequence operably linked upstream of the transcription initiation region.

18. The human-SOD-expressing vector according to claim 17 wherein the distance between the Shine-Delgarno-like sequence and the transcription initiation region is in the range of from 3 to 10 bases.

19. A shuttle vector plasmid which is able to stably transform cells of blue-green algae, comprising vector plasmid pBAS18 into which an operon comprising a structural gene encoding a physiologically active polypeptide, at least one promoter region comprising the transcription initiation region of the RuBisCO gene of *Anacystis nidulans* located upstream of the structural gene, and the transcription termination region of the RuBisCO gene located downstream of the structural gene is ligated.

20. A shuttle vector plasmid which is able to stably transform cells of blue-green algae, comprising vector plasmid pBAX18 into which an operon comprising a structural gene encoding a physiologically active polypeptide, at least one promoter region comprising the transcription initiation region of the RuBisco gene of *Anacystis nidulans* located upstream of the structural gene, and the transcription termination region of the RuBisCO gene located downstream of the structural gene is ligated.

21. A shuttle vector plasmid which is able to stably transform cells of blue-green algae, comprising vector plasmid pBAX20 into which an operon comprising a structural gene encoding a physiologically active polypeptide, at least one promoter region comprising the transcription initiation region of the RuBisCO gene of *Anacystis nidulans* located upstream of the structural gone, and the transcription termination region of the RuBisCO gene located downstream of the structural gene is ligated.

* * * * *

SEQUENCE LISTING ( 1 ) GENERAL INFORMATION:

( i i i ) NUMBER OF SEQUENCES:2

( 2 ) INFORMATION FOR SEQ ID NO: 1:

( i ) SEQUENCE CHARACTERISTICS:
        ( A ) LENGTH:320

(B) TYPE:Nucleic Acid
(C) STRANDEDNESS:Double
(D) TOPOLOGY:Linear (iv) ANTI-SENSE:No (xi) SEQUENCE DESCRIPTION:SEQ ID NO: 1:

```
CGTCCGTCGC AACGGAAGTC TCCGCTGGAC TTGCGCTGTG GGACTGCAGC TTTACAGGCT
GCAGGCAGCG TTGCCTTCAG AGGCGACCTG AACGCGACAC CCTGACGTCG AAATGTCCGA    60

CCCCCTGCCA GAAATCCTGA ATCGTCGACC ATATCTGACA TATCTCTAGG GAGAAGCTTA
GGGGGACGGT CTTTAGGACT TAGCAGCTGG TATAGACTGT ATAGAGATCC CTCTTCGAAT   120

TGGCTACCAA AGCTGTTTGC GAAATCCTGA ATCGTCGACC ATATCTGACA TATCTCTAGG
ACCGATGGTT TCGACAAACG CTTTAGGACT TAGCAGCTGG TATAGACTGT ATAGAGATCC   180

GAGAAAGCTT ATGGCTACCA GAAATCCTGA ATCGTCGACC ATATCTGACA TATCTCTAGG
CTCTTTCGAA TACCGATGGT CTTTAGGACT TAGCAGCTGG TATAGACTGT ATAGAGATCC   240

GAGAGAAGCT TATGGCTACC GAAATCCTGA ATCGTCGACC ATATCTGACA TATCTCTAGG
CTCTCTTCGA ATACCGATGG CTTTAGGACT TAGCAGCTGG TATAGACTGT ATAGAGATCC   300

GAGAGAAAGC TTATGGCTAC
CTCTCTTTCG AATACCGATG                                                320
```

(2) INFORMATION FOR SEQ ID NO: 2:

(i) SEQUENCE CHARACTERISTICS:
(A) LENGTH:1186
(B) TYPE:Nucleic Acid
(C) STRANDEDNESS:Single
(D) TOPOLOGY:Linear (iv) ANTI-SENSE:No (xi) SEQUENCE DESCRIPTION:SEQ ID NO: 2:

```
GAGCTCCCCA ATCCTCGTGA TGATCAGTGA TGGAAAAAGC ACTGTAATTC CCTTGGTTTT     60

TGGCTGAAAG TTTCGGACTC AGTAGACCTA AGTACAGAGT GATGTCAACG CCTTCAAGCT    120

AGACGGGAGG CGGCTTTTGC CATGGTTCAG CGATCGCTCC TCATCTTCAA TAAGCAGGGC    180

ATGAGCCAGC GTTAAGCAAA TCAAATCAAA TCTCGCTTCT GGGCTTCAAT AAATGGTTCC    240

GATTGATGAT AGGTTGATTC ATGAGGAATC TAAGGCTTAA TTCTCCACAA AGAATTAAG     300

CGTCCGTCGC AACGGAAGTC TCCGCTGGAC TTGCGCTGTG GGACTGCAGC TTTACAGGCT    360

CCCCCTGCCA GAAATCCTGA ATCGTCGACC ATATCTGACA TATCTCTAGG GAGAAGCTT     420

ATGGCTACCA AAGCTGTTTG CGTTCTGAAA GGTGACGGCC CGGTTCAGGG TATCATCTTC    480

GAACAGAAAG AATCTAACGG TCCGGTTAAA GTTTGGGGTT CTATCAAAGG CCTGACCGAA    540

GGTCTGCATG GATTCCATGT TCATGAATTT GGTGACAACA CTGCAGGTTG CACCTCTGCA    600

GGGCCTCATT TCAACCCGCT GTCGCGTAAA CATGGTGGGC CGAAAGACGA AGAACGTCAT    660

GTTGGTGACC TAGGTAACGT TACCGCTGAC AAAGACGGTG TCGCTGACGT TTCTATCGAA    720

GACTCTGTTA TCTCTCTGTC TGGTGACCAT TGCATCATCG GTCGTACTCT GGTTGTTCAT    780

GAAAAGCGG ATGACCTGGG TAAAGGTGGT AACGAGGAAT CTACCAAAAC CGGTAACGCT     840

GGTTCTCGTC TGGCATGCGG TGTTATCGGT ATCGCTCAGT AGTGAGGATC CCGGCCGCTA    900

CTAAAGCCTG ATTTGTCTTG ATAGCTGCTC TGCCTTTGGG CAGGGGCTTT TTTCTGTCTG    960

CCATTCTTGA GGATGGCGGA CTCTTTCCCT TTTGCTCTAC GCCCATGAAT GCGATCGCAG   1020

TCTCCCCTGT CCAGCACGTT GGAGTGATTG GTGGTGGCCA GTTAGCTTGG AGTCTGGCAC   1080

CAGCAGCGCA ACAGTTGCGG ATGTCGCTGC ACGTTCAAAC ACCCAATGAT CACGACCCAG   1140

CAGTAGCGAT CGCGGATCAA ACCGTATTGC AAGCAGTTGC TGACGC                  1186
```